United States Patent
Levenson et al.

(10) Patent No.: US 8,385,615 B2
(45) Date of Patent: Feb. 26, 2013

(54) SPECTRAL IMAGING OF BIOLOGICAL SAMPLES

(75) Inventors: Richard Levenson, Brighton, MA (US); Paul J. Cronin, Allen, TX (US); Kirk William Gossage, Milford, CT (US); Clifford C. Hoyt, Wellesley, MA (US)

(73) Assignee: Cambridge Research & Instrumentation, Inc., Woburn, MA (US)

( * ) Notice: Subject to any disclaimer, the term of this patent is extended or adjusted under 35 U.S.C. 154(b) by 979 days.

(21) Appl. No.: 12/390,690

(22) Filed: Feb. 23, 2009

(65) Prior Publication Data
US 2009/0245605 A1    Oct. 1, 2009

Related U.S. Application Data

(63) Continuation of application No. 10/573,242, filed as application No. PCT/US2004/031609 on Sep. 23, 2004, which is a continuation-in-part of application No. 10/669,101, filed on Sep. 23, 2003, now Pat. No. 7,321,791.

(51) Int. Cl.
| G06K 9/00 | (2006.01) |
| G06K 9/46 | (2006.01) |
| G06K 9/62 | (2006.01) |
| G06K 9/66 | (2006.01) |
| G01N 33/48 | (2006.01) |
| G01N 21/64 | (2006.01) |
| G01J 3/00 | (2006.01) |
| G01J 1/00 | (2006.01) |
| G01J 1/58 | (2006.01) |
| G01T 1/00 | (2006.01) |
| G21G 4/00 | (2006.01) |
| A61B 5/05 | (2006.01) |
| A61B 6/00 | (2006.01) |

(52) U.S. Cl. ......... 382/128; 382/165; 382/191; 382/224; 356/39; 356/300; 250/336.1; 250/483.1; 250/493.1; 600/407; 600/476

(58) Field of Classification Search .................. None
See application file for complete search history.

(56) References Cited

U.S. PATENT DOCUMENTS

| 4,379,233 A | 4/1983 | Rosenthal |
| 4,519,707 A | 5/1985 | Kuffer |
| 4,669,878 A | 6/1987 | Meier |

(Continued)

FOREIGN PATENT DOCUMENTS

| EP | 512965 | 11/1992 |
| WO | WO 98/43042 | 10/1998 |

(Continued)

OTHER PUBLICATIONS

Jeremy J. Andrew and Thomas M. Hancewicz, "Rapid Analysis of Raman Image Data Using Two-Way Multivariate Curve Resolution," Appl. Spectrosc. 52, 797-807 (1998).*

(Continued)

*Primary Examiner* — Randolph I Chu
*Assistant Examiner* — Nathan Bloom
(74) *Attorney, Agent, or Firm* — Fish & Richardson P.C.

(57) ABSTRACT

The invention features a method including: (i) providing spectrally resolved information about light coming from different spatial locations in a sample comprising deep tissue in response to an illumination of the sample, wherein the light includes contributions from different components in the sample; (ii) decomposing the spectrally resolved information for each of at least some of the different spatial locations into contributions from spectral estimates associated with at least some of the components in the sample; and (iii) constructing a deep tissue image of the sample based on the decomposition to preferentially show a selected one of the components.

24 Claims, 17 Drawing Sheets

U.S. PATENT DOCUMENTS

| | | | |
|---|---|---|---|
| 4,800,279 A | 1/1989 | Hieftji et al. | |
| 5,029,245 A | 7/1991 | Keranen et al. | |
| 5,042,893 A | 8/1991 | Ong | |
| 5,066,124 A | 11/1991 | Wulf | |
| 5,115,137 A | 5/1992 | Andersson-Engels et al. | |
| 5,137,364 A | 8/1992 | McCarthy | |
| 5,424,545 A | 6/1995 | Block et al. | |
| 5,433,197 A | 7/1995 | Stark | |
| 5,507,287 A | 4/1996 | Palcic et al. | |
| 5,539,517 A | 7/1996 | Cabib et al. | |
| 5,567,937 A | 10/1996 | Pinkus | |
| 5,608,213 A | 3/1997 | Pinkus et al. | |
| 5,647,368 A | 7/1997 | Zeng et al. | |
| 5,719,024 A | 2/1998 | Cabib et al. | |
| 5,760,407 A | 6/1998 | Margosiak et al. | |
| 5,827,190 A | 10/1998 | Palcic et al. | |
| 5,834,203 A | 11/1998 | Katzir et al. | |
| 5,838,451 A | 11/1998 | McCarthy | |
| 5,912,165 A | 6/1999 | Cabib et al. | |
| 5,991,028 A | 11/1999 | Cabib et al. | |
| 5,995,645 A | 11/1999 | Soenkson et al. | |
| 5,999,844 A * | 12/1999 | Gombrich et al. | 600/476 |
| 6,002,137 A | 12/1999 | Hayashi | |
| 6,007,996 A | 12/1999 | McNamara et al. | |
| 6,051,835 A | 4/2000 | Pettipiece et al. | |
| 6,075,595 A | 6/2000 | Malinen | |
| 6,142,629 A | 11/2000 | Adel et al. | |
| 6,160,617 A | 12/2000 | Yang | |
| 6,160,618 A | 12/2000 | Garner | |
| 6,232,523 B1 | 5/2001 | Tan et al. | |
| 6,235,968 B1 | 5/2001 | Tan et al. | |
| 6,236,881 B1 | 5/2001 | Zahler et al. | |
| 6,251,384 B1 | 6/2001 | Tan et al. | |
| 6,272,376 B1 | 8/2001 | Marcu et al. | |
| 6,289,229 B1 | 9/2001 | Crowley | |
| 6,300,639 B1 * | 10/2001 | Wiederhoeft | 250/458.1 |
| 6,364,829 B1 | 4/2002 | Fulghum | |
| 6,373,568 B1 * | 4/2002 | Miller et al. | 356/326 |
| 6,393,315 B1 | 5/2002 | Aprahamian et al. | |
| 6,421,131 B1 | 7/2002 | Miller | |
| 6,466,687 B1 | 10/2002 | Uppaluri et al. | |
| 6,556,853 B1 | 4/2003 | Cabib et al. | |
| 6,649,159 B2 | 11/2003 | Yang et al. | |
| 6,665,438 B1 | 12/2003 | Lin | |
| 6,690,466 B2 | 2/2004 | Miller et al. | |
| 6,690,817 B1 | 2/2004 | Cabib et al. | |
| 6,759,038 B2 | 7/2004 | Tan et al. | |
| 6,776,760 B2 | 8/2004 | Marmarelis | |
| 6,821,245 B2 | 11/2004 | Cline et al. | |
| 6,891,613 B2 | 5/2005 | Wolleschensky et al. | |
| 6,920,239 B2 | 7/2005 | Douglass et al. | |
| 6,924,893 B2 | 8/2005 | Oldenbourg et al. | |
| 6,952,499 B1 | 10/2005 | Vititoe | |
| 6,954,667 B2 | 10/2005 | Treado et al. | |
| 7,009,699 B2 | 3/2006 | Wolleschensky et al. | |
| 7,151,270 B2 | 12/2006 | Birk et al. | |
| 7,321,791 B2 | 1/2008 | Levenson et al. | |
| 7,519,206 B2 | 4/2009 | Mulet-Parada et al. | |
| 7,640,140 B2 | 12/2009 | Ruchti et al. | |
| 7,679,740 B2 | 3/2010 | Neiss et al. | |
| 7,689,023 B2 | 3/2010 | Rabinovich | |
| RE41,333 E | 5/2010 | Blank et al. | |
| 7,920,736 B2 | 4/2011 | Sammak et al. | |
| 7,945,077 B2 | 5/2011 | Demos | |
| 7,990,532 B2 | 8/2011 | Neiss et al. | |
| 8,019,134 B2 | 9/2011 | Athelogou et al. | |
| 8,116,548 B2 | 2/2012 | Zheng et al. | |
| 8,154,612 B2 | 4/2012 | Quan et al. | |
| 2002/0022766 A1 | 2/2002 | Adachi | |
| 2002/0035330 A1 | 3/2002 | Cline et al. | |
| 2003/0081204 A1 * | 5/2003 | Cronin et al. | 356/300 |
| 2003/0123056 A1 | 7/2003 | Barnes et al. | |
| 2003/0135092 A1 | 7/2003 | Cline et al. | |
| 2003/0138140 A1 | 7/2003 | Marcelpoil et al. | |
| 2003/0179372 A1 * | 9/2003 | Knebel | 356/318 |
| 2003/0223248 A1 | 12/2003 | Cronin et al. | |
| 2004/0006275 A1 | 1/2004 | Demos et al. | |
| 2004/0006276 A1 | 1/2004 | Demos et al. | |
| 2004/0081621 A1 | 4/2004 | Arndt et al. | |
| 2004/0181375 A1 * | 9/2004 | Szu et al. | 703/2 |
| 2004/0225222 A1 | 11/2004 | Zeng et al. | |
| 2005/0065406 A1 | 3/2005 | Cline et al. | |
| 2005/0065440 A1 | 3/2005 | Levenson | |
| 2005/0143627 A1 | 6/2005 | Cline et al. | |
| 2005/0171434 A1 | 8/2005 | Madden et al. | |
| 2005/0243313 A1 * | 11/2005 | Neher et al. | 356/317 |
| 2006/0074282 A1 | 4/2006 | Ward et al. | |
| 2006/0129040 A1 | 6/2006 | Fine et al. | |
| 2006/0220881 A1 | 10/2006 | Al-Ali et al. | |
| 2006/0241496 A1 | 10/2006 | Fengler et al. | |
| 2007/0015963 A1 | 1/2007 | Fengler et al. | |
| 2007/0016082 A1 | 1/2007 | Levenson et al. | |
| 2007/0080305 A1 | 4/2007 | Maitrejean et al. | |
| 2007/0135999 A1 | 6/2007 | Kolatt | |
| 2007/0249913 A1 | 10/2007 | Freeman et al. | |
| 2008/0051665 A1 | 2/2008 | Xu et al. | |
| 2008/0294032 A1 | 11/2008 | Levenson et al. | |
| 2009/0048785 A1 | 2/2009 | Katzir et al. | |
| 2010/0034453 A1 | 2/2010 | Lynch | |
| 2011/0238325 A1 | 9/2011 | Lett et al. | |

FOREIGN PATENT DOCUMENTS

| | | |
|---|---|---|
| WO | WO 98/46133 | 10/1998 |
| WO | WO 99/18847 | 4/1999 |
| WO | WO 01/11343 | 2/2001 |
| WO | WO 2005/040769 | 5/2005 |
| WO | WO 2009/006696 | 1/2009 |

OTHER PUBLICATIONS

Dickinson ME, Simbuerger E, Zimmermann B, Waters CW, Fraser SE; Multiphoton excitation spectra in biological samples. J. Biomed. Opt. 0001;8(3):329-338.*

Hiraoka, Yasushi, Takeshi Shimi, and Tokuko Haraguchi. "Multispectral imaging fluorescence microscopy for living cells." Cell structure and function 27.5 (2002): 367-374.*

Amoh, Y. et al., "Hair follicle-derived blood vessels vascularize tumors in skin and are inhibited by doxorubicin", *Cancer Res*. vol. 65, pp. 2337-2343 (2005).

Amoh, Y. et al., Nestin-linked green fluorescent protein transgenic nude mouse for imaging human tumor angiogenesis. Cancer Res. 65, 5352-5357, 2005.

Amoh, Y. et al., "Dual-color imaging of nascent blood vessels vascularizing pancreatic cancer in an orthotopic model demonstrates antiangiogenesis efficacy of gemcitabine", *J. Surgical Research*, vol. 132, pp. 164-169 (2006).

Amoh, Y. et al., "Dual-color imaging of nascent angiogenesis and its inhibition in liver metastases of pancreatic cancer", *Anticancer Research*, vol. 26, pp. 3237-3242 (2006).

P.S. Andersson et al. "Flourescence Endoscopy Instrumentation for Improved Tissue Characterization." Med. Phys. 14 (4) Jul./Aug. 1987. 633-636.

Nicholas Billinton et al., "Seeing the Wood through the Trees: A Review of Techniques for Distinguishing Green Fluorescent Protein from Endogenous Autofluorescence", *Analytical Biochemistry*, vol. 291, pp. 175-197 (2001).

K.J. Brodbeck et al. "A System for Real Time Flourescence Imaging in Color for Tumor Diagnosis." Med. Phys. 14 (4) Jul./Aug. 1987 637-639.

Kenneth R. Castleman, "Color compensation for digitized FISH images", *Bioimaging 1*, pp. 159-165 (1993).

R. Cubeddu et al., "Time-gated Fluorescence Spectroscopy and Imaging of Porphyrins and Phthalocyanines", *SPIE*, vol. 1525, pp. 17-25 (1991).

Richard O. Duda, et al., "Chapter 10—Unsupervised Learning and Clustering", *Pattern Classification*, pp. 517-599, John Wiley & Sons, Inc., New York, NY (2001).

Silvio Folli et al., "Antibody-Indocyanin Conjugates for Immunophotodetection of Human Squamous Cell Carcinoma in Nude Mice", *Cancer Research*, vol. 54, pp. 2643-2649 (May 15, 1994).

S. Folli et al. "Immunophotodiagnosis of Colon Carcinomas in Patients Injected with Flourosceinated Chimerica Antibodies Against Carcinoembryionic Antigen." Institute of Biochemistry, University of Lausanne, Switzerland. 7973-7977.
Gentry et al., Biomedical Applications of the Information-Efficient Spectral Imaging Sensor (ISIS), Gentry, SPIE vol. 3603, pp. 129-142.
David Gillis et al. "Using Endmembers as a Coordinate System in Hyperspectral Imagery." Naval Research Laboratory, Washington, DC. 1-9.
Andrew A. Green et al. "A Transformation for Ordering Multispectral Data in Terms of Image Quality with Implications for Noise Removal." IEEE Transactions of Geoscience and Remote Sensing vol. 26, No. 1 Jan. 1988. 65-74.
Jacqueline Hewett et al., "The Application of a Compact Multispectral Imaging System with Integrated Excitation Source to in vivo Monitoring of Fluorescence During Topical Photodynamic Therapy of superficial Skin Cancers", *Photochemistry and Photobiology*, vol. 73, No. 3, pp. 275-282 (2001).
Klaus B. Hilger et al. "MADCAM—The Multispectral Active Decomposition Camera." IMM, Informatics and Mathematical Modelling, Technical University of Denmark. 1-7.
Hyvarien et al., "Novel Spectroscopic Techniques for Biomedical Applications," Optoelectronics Laboratory, Finland, SPIE vol. 2084, pp. 224-230, 1994.
L.O. Jimenez et al., "High Dimensional Feature Reduction via Projection Pursuit," TR-ECE 96-5, School of Electrical Engineering, Purdue University, West Lafayette, IN 47907-1285, Apr. 1995.
Luis Jimenez et al., "Supervised Classification in High Dimensional Space: Geometrical, Statistical and Asymptotical Properties of Multivariate Data", *IEEE Transactions on Geoscience and Remote Sensing*, vol. 37, No. 6, pp. 1-32 (Nov. 1999).
Keraanen et al., "Thirty-two Channel LED Array Spectrometer Module with Compact Optomechanical Construction," Technical Research Centre of Finland, Electronics Laboratory, Finland, SPIE vol. 1533 Optomechanics and Dimensional Stability (1991), pp. 122-128.
Nirmal Keshava et al. "Spectral Unmixing." IEEE Signal Processing Magazine. Jan. 2002. 44-57.
M. Kohl et al., "Imaging of tumors by time-delayed laser-induced fluorescence", *SPIE*, vol. 1525, pp. 26-34 (1991).
David Landgrebe. "Hyperspectral Image Data Analysis." IEEE Signal Processing Magazine, Jan. 2002. 17-28.
David Landgrebe. "Information Extraction Principles and Methods for Mutispectral and Hyperspectral Image Data." School of Electrical and Computer Engineering. (1998) 1-29.
Dimitris Manolakis et al. "Detection Algorithms for Hyperspectral Imaging Applications." IEE Signal Processing Magazine. Jan. 2002. 29-43.
Jose M.P. Nascimento. "Vertex Component Analysis: A Fast Algorithm to Unmix Hyperspectral Data." 1-23, 2005.
R.A Neville et al. "Automatic Endmember Extraction from Hyperspectral Data for Mineral Exploration." Fourth International Airborne Remote Sensing Conference and Exhibition Jun. 1999. 1-8.
Andre Pelegrin et al., "Antibody-Fluorescein Conjugates for Photoimmunodiagnosis of Human Colon Carcinoma in Nude Mice", *Cancer*, vol. 67, pp. 2529-2537 (May 15, 1991).
Antonio Plaza et al. "A Quantitative and Comparitive Analysis of Endmember Extraction Algorithms from Hyperspectral Data." IEEE Transactions on Geoscience and Remote Sensing vol. 42 No. 3, Mar. 2004. 650-663.
Antonio Plaza et al. "Spatial/Spectral Endmember Extraction by Multidimensional Mophological Operations." IEEE Transactions on Geoscience and Remote Sensing vol. 40, No. 9 Sep. 2002. 2025-2041.
F.P. Seelos IV et al. "Bounded Variable Least Squares—Application of a Constrained Optimization Algorithm to the Analysis of TES Emmisivity Spectra." Lunar and Planetary Sciences XXXIV (2003) 56-69.
Shnitser et al., "Spectrally Adaptive Light Filtering," Physical Optics Corporation, Torrance, CA, SPIE vol. 3140, pp. 117-127, 1997.
B.R. Stallard, Construction of Filter Vectors for the Information-Efficient Spectral Imaging Sensor, Imaging Spectroscopy IV, Proc. SPIE, vol. 3438, pp. 172-182, San Diego, 1998.
David W. J. Stein et al. "Anomaly Detection from Hyperspectral Imagery." IEEE Signal Processing Magazine. Jan. 2002. 58-69.

Karatina Svanberg et al., "Fluorescence Studies of Hematoporphyrin Derivative in Normal and Malignant Rat Tissue", *Cancer Research*, vol. 46, pp. 3803-3808 (Aug. 1986).
W.C. Sweatt et al., "ISIS; An Information-Efficient Spectral Imaging System," Imaging Spectrometry IV, Proc. SPIE, vol. 3438, pp. 98-106, San Diego, 1998.
Tamara Troy et al. "Quantitative Comparison of the Sensitivity of Detection of Flourescent and Bioluminescent Reporters in Animal Models." Molecular Imaging vol. 5 No. 1, Jan. 2004. 9-23.
Eric Van Leengoed et al., "Tissue-Localizing Properties of Some Photosensitizers Studied by in vivo Fluorescence Imaging", *Journal of Photochemistry and Photobiology, B: Biology*, vol. 6, pp. 111-119 (1990).
G. Wagnieres et al., "Photodetection of Early Cancer in the Upper Aerodigestive Tract and the Bronchi using Photofrin II and Colorectal Adenocarcinoma with Fluoresceinated Monoclonal Antibodies", *SPIE*, vol. 1525, pp. 219-236 (1991).
Stefan Wild et al. "Motivating Non-Negative Matrix Factorizations." Department of Applied Mathematics, University of Colorado, 1-11.
Michael E. Winter. "Fast Autonomous Spectral Endmember Determination in Hyperspectral Data." 13th Internation Conference on Applied Geologic Remote Sensing, Mar. 1-3, 1999. 1-16.
Michael E. Winter. "N-FINDR: An Algorithm for Fast Autonomous Spectral End-Member Determination in Hyperspectral Data." Department of Earth Sciences. 1-8, 1999.
Yang, M. et al., "Whole-body and intravital optical imaging of angiogenesis in orthotopically implanted tumors", *Proc. Natl. Acad. Sci. USA*, vol. 98, pp. 2616-2621 (2001).
Yang, M. et al., "Direct external imaging of nascent cancer, tumor progression, angiogenesis, and metastasis on internal organs in the fluorescent orthotopic model", *Proc. Natl. Acad. Sci. USA*, vol. 99, pp. 3824-3829 (2002).
Yang, M. et al., "Dual-color fluorescence imaging distinguishes tumor cells from induced host angiogenic vessels and stromal cells", *Proc. Natl. Acad. Sci. USA*, vol. 100, pp. 14259-14262 (2003).
Yang, M. et al., "Transgenic nude mouse with ubiquitous green fluorescent protein expression as a host for human tumors", *Cancer Research*, vol. 64, pp. 8651-8656 (2004).
Yang, M. et al., "Whole-body subcellular multicolor imaging of tumor-host interaction and drug response in real time", *Cancer Res.*, vol. 67, pp. 5195-5200 (2007).
Yang, M. et al., "Facile whole-body imaging of internal fluorescent tumors in mice with an LED flashlight", *BioTechniques*, vol. 39, pp. 170-172 (2005).
European Search Report for Application No. 06014263.5-2305 dated Oct. 10, 2007.
Selim Aksoy et al., "Textural Features for Image Database Retrieval", IEEE, pp. 45-49 (1998).
Bishop, Christopher M., "The Multi-Layer Perceptron", Neural Networks for Pattern Recognition (Oxford University Press, 1995), pp. 116-163.
Kenneth P. Camilleri et al., "Spectral Unmixing of Mixed Pixels for Texture Boundary Refinement", IEEE, pp. 1084-1087 (2000).
Haralick, R.M. et al., "Textural features for image classification", IEEE Transactions on Systems, Man, and Cybernetics, vol. SMC-3: 610-621 (1973).
Jimenez, L. et al., "Hyperspectral Data Analysis and Feature Reduction Via Projection in Pursuit", IEEE Transactions on Geoscience and Remote Sensing 37(6): 2653-2667 (1999).
Paul M. Mather, "Classification 'What is or is not a cow is for the public to decide'", Computer Processing of Remotely-Sensed Images: An Introduction, Third Edition, John Wiley & Sons, Ltd. (2004).
Stephen W. Wharton, "A Contextual Classification Method for Recognizing Land Use Patterns in High Resolution Remotely Sensed Data", Pattern Recognition, vol. 15, No. 4, pp. 317-324 (1982).

* cited by examiner

SPECTRAL IMAGING OF BIOLOGICAL SAMPLES

CROSS-REFERENCE TO RELATED APPLICATIONS

This application is a continuation of and claims priority under 35 U.S.C. §120 to U.S. application Ser. No. 10/573,242, filed Mar. 22, 2006, which claims priority to WIPO Application Serial No. PCT/2004/031609, filed Sep. 23, 2004, which claims priority to U.S. application Ser. No. 10/669,101, filed on Sep. 23, 2003. The contents of the prior applications are incorporated herein by reference in their entirety.

BACKGROUND

Optical imaging of deep tissue is used to probe structures within biological specimens for laboratory research and biomedical purposes. This includes the imaging of internal organs and subdermal tissue in animals such as mice, zebrafish, or humans, and one of the goals is to learn about internal structures without surgery or other intrusive measures.

In one technique of deep tissue imaging, fluorescent agents which are associated with a specific target in the specimen are imaged by exciting them with illumination light, causing them to fluoresce; the fluorescent emission is separated from the illumination light, which has a different wavelength, by barrier filters and then is detected using a very sensitive camera such as a cooled CCD detector. In other techniques, the specimen is modified using agents that cause it to produce material that is inherently fluorescent, with the most common example being green fluorescent protein (GFP). Further techniques involve use of quantum dots as luminous probes.

As used herein, compounds such as fluorescent dyes, fluorescent proteins such as GFP, quantum dots, surface-enhanced Raman reagents, as well as related compounds or others used for similar purposes, are all examples of a "target compound" of a measurement.

The signals produced in such experiments are typically weak. In general, robust detection of the weak levels of light emitted from the deep structures is beneficial because it provides earlier, or more reliable, detection of the structures being studied. Also, it may enable detection of lower levels of the target compound. Accordingly, techniques or apparatus used for deep tissue imaging are valued if they offer a low detection threshold.

SUMMARY

The inventors have recognized that one can successfully use spectral discrimination techniques to accurately image one or more target compounds in a deep tissue sample, such as a subdermal tissue or an organ in an animal or a human. For example, one collects spectrally resolved information about light coming from different spatial locations in a sample, and then decomposes the spectrally resolved information into contributions from estimates of the pure spectra corresponding to different components in the sample (e.g., autofluorescence and one or more target compounds). This decomposition can be used to reconstruct one or more images that preferentially show a selected component. The spectrally resolved information typically corresponds to a spectral image cube in which each pixel includes a sample emission spectrum coming from a corresponding spatial location.

The inventors have also developed algorithms that are particularly useful for estimating the pure spectrum of one or more of the sample components from such spectral image cube data, even where one or more of the components are only present in a mixed form (i.e., light from one components overlaps both spatially and spectrally with light from another component). These pure spectra can then be used in the decomposition of the spectral image cube data into selected component images. These algorithms are useful not only for deep tissue samples, but for biological samples in general. Moreover, in some embodiments the algorithms require little or no user input.

In some embodiments, the algorithms recognize that an accurate estimate for the pure spectrum of a first component that is only present in the image cube in mixed form can be determined by using at least part of the image cube data and a separate estimate for the pure spectrum of at least a second component present in the mixture. The estimate of the pure spectrum for the second component can be based on other parts of the image cube data or from prior knowledge. In the simplest example, a scaled amount of the spectral estimate for the second component is subtracted from the mixed signal spectrum to reveal an estimate for the pure spectrum of the first component. For example, the scaling can be set to achieve small, but non-zero signal values in each spectral channel.

We now generally summarize at least some of the different aspects and features of the invention.

In general, in one aspect, the invention features a method including: (i) providing spectrally resolved information about light coming from different spatial locations in a sample (e.g., a deep tissue sample) in response to an illumination of the sample, wherein the light includes contributions from different components in the sample; and (ii) constructing an image of the sample based on the spectrally resolved information to preferentially show a selected one of the components. Typically, the spectrally resolved information includes information corresponding to at least three, and preferably four or more, different spectral weighting functions (e.g., different spectral bands).

The method may further include decomposing the spectrally resolved information for each of at least some of the different spatial locations into contributions from a spectral estimate associated with each of at least one or more of the components in the sample. The construction of the image may be based on this decomposition. Also, one or more of the spectral estimates may be estimates of the pure spectra for the components. The pure spectrum of a given component corresponds to the spectrally resolved information that would be observed if only that component contributes to the light being measured (for a given spatial location).

The method may further include any of the following features.

The spectrally resolved information may include information about a set of images in which the light coming from the sample is spectrally filtered, wherein the spectral filtering for each image corresponds to a different spectral weighting function.

The spectrally resolved information may include information about a set of images in which light used to illuminate the sample is spectrally filtered, wherein the spectral filtering for each image corresponds to a different spectral weighting function.

The different spatial locations typically correspond to common pixels in the set of images. The different spectral weighting functions can correspond to different spectral bands. There may three, or more preferably, four or more, images in the set of images.

The information about the set of images may include a series of values at each of the pixels, wherein each value is related to an intensity of the light coming from the sample with respect to a corresponding one of the spectral weighting functions. The spectrally resolved information for each spatial location typically includes information corresponding to at least three, and more preferably, four or more different spectral weighting functions.

The spectrally resolved information may include a spectral image cube.

The light coming from the sample may include fluorescence from the sample, reflectance, phosphorescence, scattering, or Raman scattering from the sample, or it may include light transmitted through the sample.

At least one of the components may relate to autofluorescence.

At least one of the components may include a target compound (e.g., a fluorescent protein or a quantum dot). For example, the selected component may be the component including the target compound.

The method may further include illuminating the sample and collecting the spectrally resolved information. For example, collecting the spectrally resolved information may include using a liquid crystal tunable spectral filter, an acousto-optical tunable spectral filter, a set of spectral filters, a spectral filter wheel, a dispersive prism, a grating, a spectrometer, or monochromator.

The image of the selected component may includes an image in which signal from the other components is reduced relative to signal from the selected component.

The method may further include constructing a second image of the sample based on the decomposition to preferentially show a second one of the components. The method may also include constructing a third image of the sample based on the decomposition to preferentially show a third one of the components.

The sample may be a living organism (e.g., a mammal).

The sample may include deep tissue, tissue slices, cells, subdermal tissue, or a microscope slide carrying biological material.

Constructing the image based on the decomposition may include constructing the deep tissue image based on the contributions at different spatial locations of the spectral estimate associated with the selected component.

The decomposition may be a linear decomposition. For example, the decomposition may include solving at least one component of a matrix equation in which one matrix in the equation is based on the spectrally resolved information and another matrix in the equation is based on the spectral estimates.

At least one of the spectral estimates may be provided independently of the spectrally resolved information.

At least a first one of the spectral estimates for a first one of the components may be determined from the spectrally resolved information. For example, all of the spectral estimates may be determined from the spectrally resolved information. The spectral estimates may be determined from the spectrally resolved information by using an unsupervised classification technique or a supervised classification technique. One example of an unsupervised classification technique includes averaging the spectrally resolved information for multiple ones of the spatial locations. One example of a supervised classification technique determining the first spectral estimate from the spectrally resolved information a region including one or more of the spatial locations, wherein the region is associated with the first component.

The first spectral estimate may be derived from the spectrally resolved information from a first set of one or more spatial locations in which the light includes contributions from multiple ones of the components. In such case, the first spectral estimate can be derived from the spectrally resolved information from the first set of spatial locations and a spectral estimates for a second one of the components.

For example, deriving the first spectral estimate may include calculating a remainder spectrum based on the spectrally resolved information from the first set and the spectral estimate for the second component. The remainder spectrum can be calculated at each of one or more of the spatial locations in the first set of spatial locations. Alternatively, the remainder spectrum can be calculated based on an average of the spectrally resolved information in the first set of spatial locations and the spectral estimate for the second component.

The spectral estimate for the second component may be derived from the spectrally resolved information. For example, the spectral estimate for the second component may be determined from the spectrally resolved information by using an unsupervised classification technique, such as averaging. Alternatively, the spectral estimate for the second component may be derived from a region including one or more of the spatial locations, wherein the region is associated with the second component.

Deriving the first spectral estimate may includes adjusting values corresponding to the spectrally resolved information for the first set of spatial locations to remove a contribution (e.g., a maximal contribution) from the second component based on the spectral estimate for the second component. The maximal contribution may be based on an error function analysis of signal in each spectral channel of the adjusted values. For example, the error function analysis tends to maintain nonnegative signal in each spectral channel of the adjusted values.

For example, the values may include a series of at least some of the values for each of the spatial locations in the first set, and removing the contribution from the second component based on the spectral estimate for the second component may include subtracting an optimized quantity of the spectral estimate for the second component from each of the series of values.

The optimized quantity for at least a first of the series of values may be based on minimizing an error function of a difference spectrum that includes a difference between the first series values and the quantity to be optimized multiplied by the spectral estimate for the second component, wherein the error function is minimized over the spectral channels. The difference spectrum may further include a constant that is also optimized over the spectral channels. The error function typically favors positive values of the difference spectrum over negative values of the difference spectrum. For example, one useful error function is includes $(e^{-\Delta}+1)\Delta^2$, where $\Delta$ is the difference spectrum. The error function may also be normalized by the magnitudes of the first series of values and the spectral estimate for the second component.

The decomposition may include: (i) a first decomposition of the spectrally resolved information at multiple spatial locations into contributions from initial spectral estimates associated with at least some of the components in the sample; (ii) improving an accuracy of at least some of the initial spectral estimates based on the first decomposition; and (iii) at least a second decomposition of the spectrally resolved information at multiple spatial locations into contributions from the improved spectral estimates.

In another aspect, the invention features an apparatus including: (i) a sample holder configured to support a sample (e.g., a deep tissue sample); (ii) an illumination source to illuminate the sample; a detector positioned to detect light from the sample; and (iii) an electronic processor coupled to the detector. The electronic processor is configured to implement any of the method steps described above, including interacting with a user as necessary.

The apparatus may further include a spectral filtering means positioned between the sample and the detector. For example, the spectral filtering means may include a liquid crystal tunable spectral filter, an acousto-optical tunable spectral filter, a set of spectral filters, a spectral filter wheel, a dispersive prism, a grating, a spectrometer, or monochromator.

Alternatively, or in addition, the apparatus may include a spectral filtering means positioned between the illumination source and the sample.

Also, the illumination source itself may provide tunable excitation light. For example, it may be a multispectral diode or LED array.

In general, in yet a further aspect, the invention features a method including: (i) providing a set of images of spectrally filtered radiation emitted from a biological sample in response to an illumination, wherein the sample includes a component supporting a target compound, the emitted radiation includes emission from the target compound and emission from one or more additional components in the sample, and each image corresponds to a different spectral weighting function for a common set of pixels; and (ii) processing the images of the spectrally filtered radiation to construct an output image of the sample in which signal from the additional components is reduced relative to signal from the target compound. The processing includes calculating a remainder spectrum for one or more pixels in the set of images based on an estimate for an emission spectrum of at least one of the components.

In yet another aspect, the invention features a method including: (i) illuminating a sample to cause the sample to emit radiation, wherein the sample includes deep tissue supporting a target compound, and wherein the emitted radiation includes emission from the target compound and emission from one or more other components in the sample; (ii) spectrally filtering the emitted radiation with each of a plurality of different spectral weighting functions; (iii) storing an image of the spectrally filtered radiation for each of the spectral weighting functions; and (iv) processing the stored images to construct a deep tissue image of the sample in which signal from the other compounds is reduced relative to signal from the target compound.

In another aspect, the invention features a method including: (i) providing a plurality of images of spectrally filtered radiation emitted from a sample in response to an illumination, wherein the sample includes deep tissue supporting a target compound, wherein the emitted radiation includes emission from the target compound and emission from one or more other components in the sample, and wherein each image corresponds to a different spectral weighting function; and (ii) processing the images of the spectrally filtered radiation to construct a deep tissue image of the sample in which signal from the other compounds is reduced relative to signal from the target compound.

In yet another aspect, the invention features an apparatus including a computer readable medium which stores a program that causes a processor to: (i) receive a plurality of images of spectrally filtered radiation emitted from a sample in response to an illumination, wherein the sample includes deep tissue supporting a target compound, wherein the emitted radiation includes emission from the target compound and emission from one or more other components in the sample, and wherein each image corresponds to a different spectral weighting function; and (ii) process the images of the spectrally filtered radiation to construct a deep tissue image of the sample in which signal from the other compounds is reduced relative to signal from the target compound.

In yet another aspect, the invention features an apparatus comprising: (i) a sample holder configured to hold a sample including deep tissue, wherein the deep tissue supports a target compound; (ii) an illumination source configured to illuminate the sample to cause it to emit radiation, wherein the emitted radiation includes emission from the target compound and emission from one or more other components in the sample; (iii) an imaging system configured to image the emitted radiation to a detector; (iv) a tunable spectral filter configured to spectrally filter the emitted radiation with each of a plurality of different spectral weighting functions; (v) a detector configured to store an image of the spectrally filtered radiation for each of the spectral weighting functions; and (vi) a electronic processor configured to process the store images to construct a deep tissue image of the sample in which signal from the other compounds is reduced relative to signal from the target compound. For example, the sample holder may configured to hold an animal, such as a mammal, like a mouse, rabbit, or human. Also, for example, the imaging system may have a demagnification greater than or equal to 1, and, for example, the imaging system may be configured to image a field of view having a diagonal dimension greater than about 2 cm onto the detector.

Embodiments of these various aspects may include any of the following features.

The sample including the deep tissue may be a living organism, such as an animal or a mammal. For example, the animal may include a mouse, a rabbit, a zebrafish, or a human. Also, the deep tissue may be an internal organ of the living organism, and the deep tissue may lie within about 2 mm or more of the living organism.

The deep tissue may be subdermal tissue.

The emission from the other components of the sample may include autofluorescence from tissue overlying the deep tissue.

The emission from the other components of the sample may include autofluorescence from one or more layers of tissue in the sample different from a layer of tissue including the deep tissue.

The target compound may be any of, for example, a fluorescent probe bound to at least a portion of the deep tissue, a quantum dot bound to at least a portion of the deep tissue, a green fluorescent protein (GFP) bound to at least a portion of the deep tissue, a yellow fluorescent protein (YFP) bound to at least a portion of the deep tissue, and a red fluorescent protein (RFP) bound to at least a portion of the deep tissue.

The emission from the target compound may be fluorescence.

At least some of the spectral weighting functions may correspond to particular wavelength bands. For example, all of the spectral weighting functions correspond to particular wavelength bands. Alternatively, at least some of the spectral weighting functions may correspond to sinusoidal weightings of multiple wavelength bands.

The spectral filtering may include using any of a liquid-crystal, tunable optical filter, an interferometric optical filter, and a filter wheel containing a plurality of band pass filters.

Each stored image may include an intensity value for each of multiple pixels.

Processing the stored images may include constructing the deep tissue image based on a weighted superposition of signals in the stored images.

Processing the recorded images may include constructing the deep tissue image based on the recorded images and at least one emission spectrum for the other components in the sample. For example, constructing the deep tissue image may include calculating a remainder spectrum for each pixel in the set of stored images based on the at least one emission spectrum for the other components.

Similarly, processing the recorded images may include constructing the deep tissue image based on the recorded images and an emission spectrum for the target compound. For example, constructing the deep tissue image may include calculating a remainder spectrum for each pixel in the set of stored images based on the emission spectrum for the target compound.

Also, processing the recorded images may include constructing the deep tissue image based on the recorded images, at least one emission spectrum for the other components in the sample, and an emission spectrum for the target compound. For example, constructing the deep tissue image may include solving at least one component of a matrix equation in which one matrix is based on the stored images, and another matrix is based on the emission spectra.

The deep tissue may support multiple target compounds and processing the stored images may include constructing a deep tissue image for each of the target compounds. For example, processing the recorded images may include constructing the deep tissue images based on the recorded images and emission spectra for the target compounds. Furthermore, processing the recorded images may include constructing the deep tissue images based on the recorded images, the emission spectra for the target compounds, and at least one emission spectrum for the other components in the sample.

The plurality of the different spectral weighting functions may include four or more spectral weighting functions.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control.

Other features, objects, and advantages of the invention will be apparent from the following detailed description.

DESCRIPTION OF DRAWINGS

The invention will now be further described merely by way of example with reference to the accompanying drawings.

DETAILED DESCRIPTION

Overview

Figure 1:
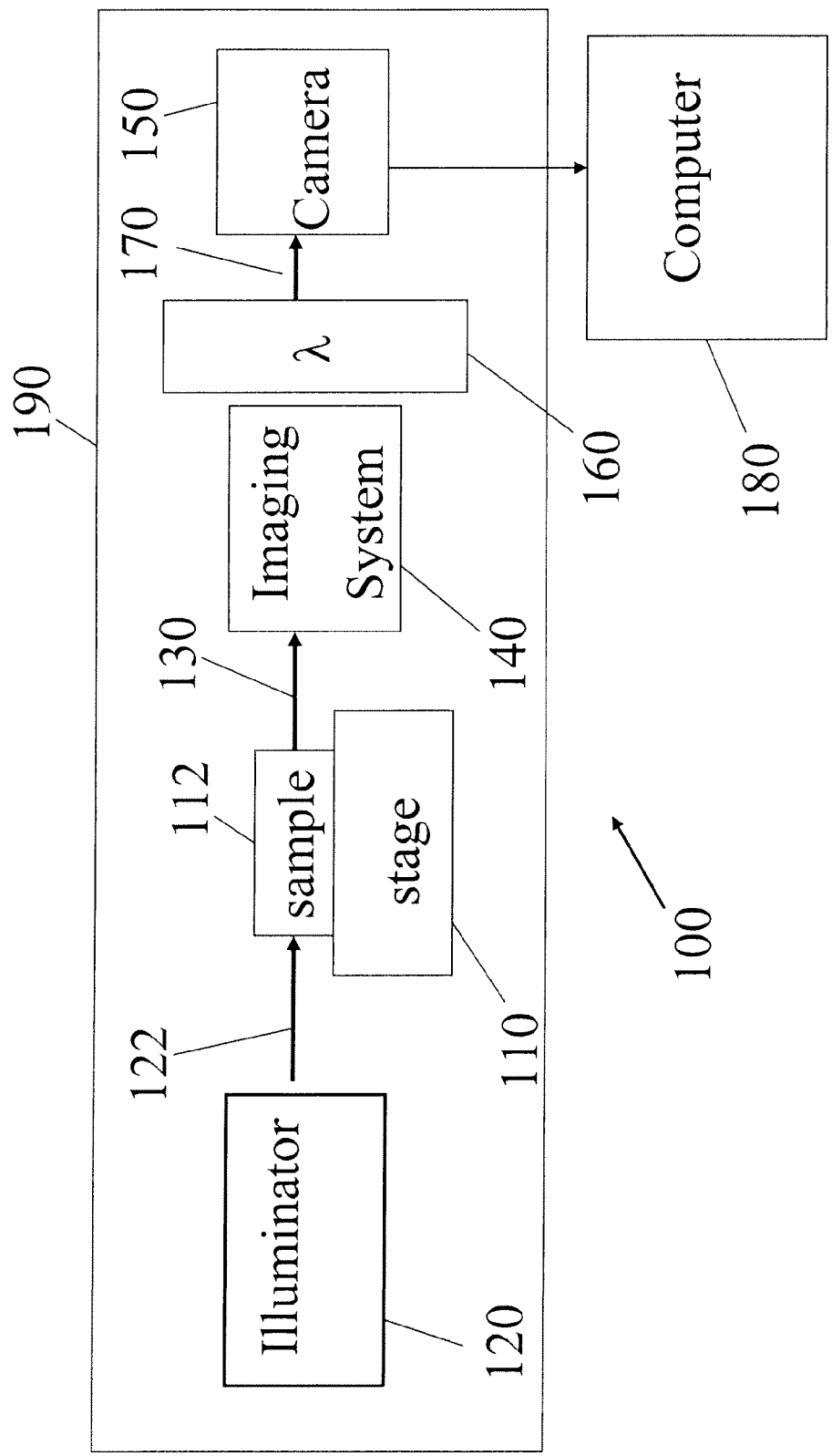
FIG. 1 is a schematic diagram of a spectral imaging system.

The invention features methods and apparatus for reducing the detection sensitivity level of a target compound in a biological sample (including deep tissue in the sample) through spectral discrimination. This involves measuring spectrally resolved information about the light coming from each of multiple spatial locations in the sample. Sometimes, the data is referred to as an "image cube," with the spectrally resolved information corresponding to values along one dimension of the cube and the spatial locations (or pixels) corresponding to the other two dimensions of the cube. Beneficial result can be obtained despite low light levels typical for deep tissue imaging. Furthermore, algorithms for processing spectrally resolved image data are disclosed that are useful not only for deep tissue imaging, but for processing spectrally resolved image data of biological samples in general. In some cases, the processing can proceed in a highly automated fashion, without little or no user-guidance, while still producing accurate images of one or more selected components in the biological sample.

Spectral imaging techniques (e.g., fluorescence imaging) can be used with samples that are labeled with fluorescent tags or are genetically modified so that one or more target compounds fluoresce or which are simply targets that fluoresce. This fluorescence from one or more target compounds is called "target fluorescence." However, in addition to components such as the target compounds, a sample may include other components that each emits radiation according to a corresponding emission spectrum. For example, there may be other compounds or materials in a sample that are not labeled or are not genetically modified that may also fluoresce at some level. This unknown and/or background fluorescence is called "autofluorescence."

This autofluorescence interferes with quantitative measurements of target fluorescence, and in some cases can be many times brighter than the target fluorescence. Some particular applications of interest are in the life sciences, including in-vivo fluorescence imaging, and fluorescence microscopy; however, the techniques described here are also effective in other applications such as bright-field microscopy. Autofluorescence can also include other spectral signatures such as instrument spectral responses, or absorptions from other constituents or chromaphores in transmitted light (e.g., bright-field) applications. Moreover, there may be multiple components, each of which give rise to different autofluorescence spectra.

Autofluorescence typically has emission spectra that differ from the target fluorescence emission spectra, providing an opportunity to apply spectral unmixing techniques to separate the target fluorescence from autofluorescence in each detected signal spectrum at a pixel in a detected image cube. In other words, the signal spectrum can be decomposed into separate contributions from the target fluorescence and the autofluorescence. This spectral unmixing produces a high contrast image of the labeled or genetically modified portion of the sample by removing the portion of a detected signal that can be attributed to autofluorescence. In some cases, more than one compound is labeled or modified with the goal being to produce multiple images representing concentrations of each target compound isolated from the autofluorescence and the other target compounds.

To accurately apply spectral unmixing tools, it is useful to obtain the pure emission spectrum of each target compound and of each autofluorescence component that may contribute to an overall detected spectrum. The more accurately the spectral shapes of such component spectra are known, the more accurately the mixed signal spectra in the image cube can be unmixed or decomposed to generate individual images representing quantities of target compounds and/or autofluorescence components. The pure emission spectrum for a given component is the signal spectrum that would be measured if only that component contributed to the measured light, such as, for example, if that component were isolated from the other components.

However, rarely are the target compound spectra represented in their "pure" form within a signal spectrum at a given pixel of the detected image cube. In some cases, published spectra of various fluorescent labels can be used. For accurate results in these cases, the system responses should be calibrated out of the system being used, as well as the system on which that the spectra were originally measured. Another way to obtain the spectra from each target compound is to individually isolate each target compound and collect the spectrum of each on the same system to be used for subsequent in-vivo experiments. However, this isolation of target compounds is often impractical. Also, the spectra resulting from labels often change when the labels are in in-vivo samples, making spectra collected from target compounds isolated from the in-vivo sample inaccurate.

In some cases it is useful to process a sample in its current state without a priori knowledge of the component spectra represented within the signal spectra of an image cube obtained from the sample. Therefore it is useful to be able to accurately determine the individual component spectra based on the image cube data so that spectral unmixing can be performed and images of individual target compounds can be generated. Techniques described below, such as the "remainder techniques," are particularly well suited for biological samples due to the typical characteristics of the component spectra involved, as described in more detail below.

Another useful aspect of these techniques described below is their compatibility with automation techniques. For example, in some implementations, it is not necessary to have a user visually identify features in an image based on specialized knowledge. In other implementations an unskilled user can provide feedback based on an initial automated step.

Imaging System

A schematic diagram of a spectral imaging system 100 for imaging biological samples is shown in FIG. 1. System 100 includes a sample holder 110 suitable for holding a specimen 112. For example, the specimen 112 may be a living organism, such as an animal or mammal. A target compound is associated with (e.g., bound to or accumulated in) selected portions of tissue (e.g., deep tissue) in the specimen 112. An illuminator 120 (e.g., a metal halide lamp or other lamp, a laser, an light emitting diode array, or any other source of electromagnetic radiation) directs excitation light 122 to the specimen 112 to excite emission (e.g., fluorescence) from the target compound in the tissue. Typically, the excitation light will also cause the autofluorescence from the other components in the specimen 112. Therefore, the electromagnetic radiation 130 emitted from the specimen 112 includes emission from the target compound as well as autofluorescence. Emitted radiation 130 is collected by imaging system 140 and imaged onto a camera 150.

Because system 100 is designed to be able to image deep tissue in relatively large specimens (e.g., living organisms), the imaging system typical provides a demagnification of one or more, or even 2 or more. That is, the image on the camera is the same size or smaller than the object field of view for the imaging system. Also, the object field of view for the imaging system is typically greater than about 2 cm (or greater than about 3 cm) along a diagonal dimension.

Furthermore, although FIG. 1 shows emitted radiation 130 as being collected from an opposite side of the specimen 112 relative to excitation light 122, in other embodiments, the emitted radiation can be collected from the same side as, or at an angle to, that illuminated by the excitation light. Moreover, illumination may be provided from multiple sides of the specimen 112.

Positioned between the specimen 112 and camera 150 is a tunable optical filter module 160 (e.g., a liquid crystal, tunable optical filter, an interferometric optical filter, or a motorized filter wheel). Optical filter module 160 spectrally filters emitted radiation 130 according to each of a plurality of spectral weighting functions (for example, four or more spectral weighting functions). The spectral weighting functions may correspond to specific wavelength bands, or may be more complicated functions such as a sinusoid distribution of pass bands. The optical filter module 160 may also optionally include other filters including, for example, a filter that reduces the amount of excitation light 122 that can enter the camera 150. Camera 150 records images of the spectral filtered emitted radiation 170 for each of the different spectral weighting functions, and sends the image data to a computer 180 for analysis. As described in greater detail below, the computer processes the image data based on the different spectral weighting functions, and one or more emission spectra corresponding to pure target compound, pure autofluorescence of one or more other components of the specimen 112, or both, to construct an image that suppresses the autofluorescence signal to reveal the target compound.

In some implementations, a portion of the system 100 (e.g., the portion of the system 100 between the illuminator 120 and the camera 150, inclusive) is optionally enclosed in a housing 190, for example, to reduce the amount of stray light (e.g., room light) that can be imaged onto the camera 150 or that can interact with the specimen 112.

Spectral Imaging Techniques

In what follows, we describe the context for the spectral imaging of the biological samples, specific examples including deep tissue imaging, and spectral unmixing techniques for constructing the images.

Signal Strength

It is a hallmark of imaging structures in biological samples (and particularly in deep-tissue samples) via target compounds that the optical signals are relatively weak. Accordingly, many practitioners place prime importance on the properties of the detector, and on the efficiency of all elements in the optical path, such as the lenses and the blocking filter used to block the excitation light from reaching the detector. Yet while the present art of CCD detectors and the like is suitable for detecting low light level signals, it does not adequately address the problem of discriminating between light emitted by the target compound, and light from other sources such as autofluorescence. Thus one's detection level in practice may be set by the level of confounding light arising from sites elsewhere within the specimen, rather than considerations such as readout noise in one's detector, or the light gathering power of the objective.

Put more precisely, one's detection limit can be seen as the greater of one's detector noise or the confounding signal flux which is presented to the detector; expressed in either case as the equivalent concentration of target compound in the specimen to produce light of that signal level at the detector.

Unless the light emitted by the target compound dominates over all other sources in the specimen, one is often limited by the confounding signal rather than by one's detection apparatus. Some level of autofluorescence is inherent in biological samples when they are illuminated with light of visible range, especially when the light is green (550 nm) or shorter. So despite the use of optimized target compounds, autofluorescence arising at or near the specimen surface can often set the detection limit.

Further, emission from target compounds within deep tissue can be attenuated by scattering or absorption as it travels from the site of emission to the surface of the specimen. The signal level reaching the imaging system is thus reduced, while light that is generated at the surface layer of the specimen is not similarly attenuated. The details of this effect depend on the geometry of the sample specimen relative to the collection optics, as well as the optical properties of the sample.

Likewise, the illumination light may be attenuated or scattered as it travels from the source of illumination through the surface layers of the specimen on its way to the structure being imaged. The excitation signal reaching the target site is reduced, while the signal developed at the surface of the specimen is not similarly attenuated. The details of this depend on the geometry of the illumination and collection optics, as well as on the optical properties of the sample specimen.

These considerations can exacerbate the effect of autofluorescence by increasing the relative contribution of autofluorescence emission to the detected signal, compared with emission from the target compound.

Figure 2:
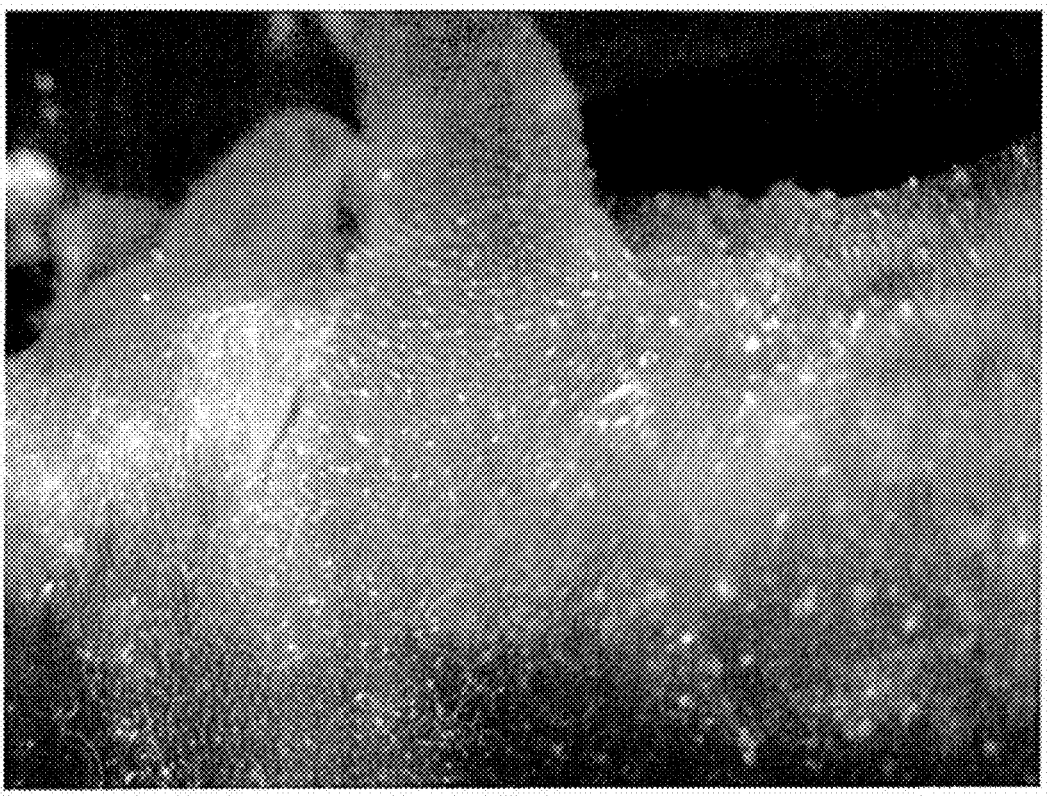
FIG. 2 is an image of a mouse which has been implanted with a fluorescently labeled tumor, imaged at a single spectral band of $\lambda=530$ nm.

The magnitude of the problem is illustrated by FIG. 2, which is an image of the fluorescent emission from a mouse. The mouse was illuminated with light of approximately 480 nm, and the emission light was filtered by a 25 nm bandpass filter centered at 530 nm. There is a tumor in the lung of the mouse which expresses the green fluorescent protein (GFP). Yet the tumor is not easily distinguishable in the image due to an equal or greater signal from generalized autofluorescence, apparently developed in the dermal layers of the mouse. As a result, while the signal level at any point in the image is easily quantified, the presence of target compound, and thus the tumor, cannot be confirmed due to high levels of background autofluorescence which sets an equal or higher detection threshold than the target compound involved.

Autofluorescence is also variable from specimen to specimen and can be unpredictable. Thus if an absolute flux level is used to make assessments about the target compound, one can obtain false positive readings. Variability can arise from factors such as mold or disease on the skin of the specimen. These are typically not uniform across the specimen. So if one seeks to detect the presence of a target compound by comparing local signal levels in a given region against the mean level for the specimen, results are also not reliable.

Spectral Crosstalk

It is possible in some cases to reduce autofluorescence by choice of the illumination wavelength. Generally the use of longer wavelengths for illumination is beneficial, as is known in the art, since they typically generate less autofluorescence. Also, it can be beneficial to choose a target compound whose emission light occurs at a different wavelength range from the autofluorescence of the specimen. Yet it is typically not possible to choose an illumination wavelength such there is no crosstalk. In the example shown in FIG. 3, the emission spectra of the target compound, GFP (shown by the darkshaded line), and of the autofluorescence (shown by the lightshaded line), are overlapping. At any wavelength where the target has substantial emission, the autofluorescence is also strong, so autofluorescence cannot be eliminated by use of a fixed optical filter or something similar. Nor does a color camera discriminate between two such similar green spectra.

Figure 3:
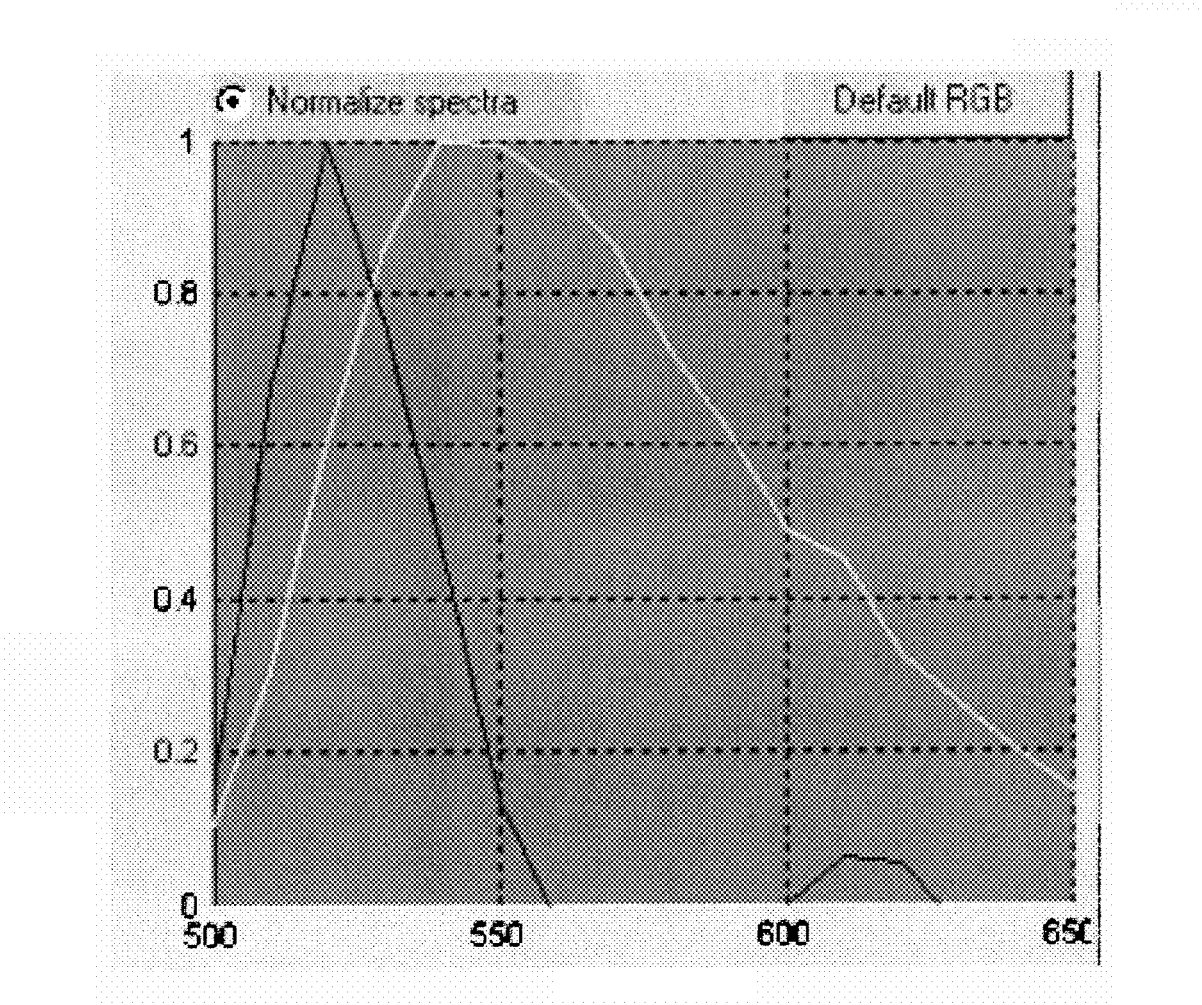
FIG. 3 is a graph of the emission spectrum of autofluorescence and the estimated emission spectrum of the target compound for the sample of FIG. 2, with the light-colored line showing the spectrum for the autofluorescence and the dark-colored line showing the estimated spectrum for the target compound.

Yet as FIG. 3 indicates, the spectra of GFP and autofluorescence emissions are nonetheless different. Thus, a spectral imaging approach can distinguish the two and eliminate or greatly reduce the contribution of the latter signal.

Spectral Unmixing

One tool for separating each pixel's signal spectrum into its component spectra is linear decomposition or unmixing. For example, one can perform a least-squares best fit approximation to determine how much of each individual component spectrum would be required to most accurately recreate the measured signal spectrum.

Spectral unmixing uses a set of input spectra to represent the component spectra within the detected image cube. Typically, the input spectra are estimates of the pure spectra for the different components. One approach for providing input spectra for unmixing, if the component spectra are not available from a library, or have not already been collected from isolated component materials, is to assume that each of the individual component spectra can be represented by the spectrum of a pixel or groups of pixels within the image cube.

However, this approach typically produces a poor estimate for at least one or more of the pure spectra. For example, rarely do the target fluorescence components exist by themselves, separate from the autofluorescence components, in isolated areas within an image cube. The signal spectrum for a region of pixels in which a target compound appears is usually a mixture of component spectra. Therefore, if one estimates the pure spectrum for one of the target components based on such a region, the unmixing will be poor—it will represent mixtures of compounds associated with the mixed component spectra.

Also, in some cases it is difficult to know a priori how many actual fluorescing components (each associated with a corresponding component spectrum) exist within a sample, in order to accurately apportion the measured signal within the image cube. If some component spectra are not represented during unmixing then the relative ratios of the remaining components will not be accurately determined.

In some cases, manually choosing from where to select the input spectra and choosing how many input spectra to unmix can work if the user can make an educated guess based on specialized knowledge and/or experience. Some users can work effectively this way if they have significant a priori knowledge of the sample.

Figure 4A:
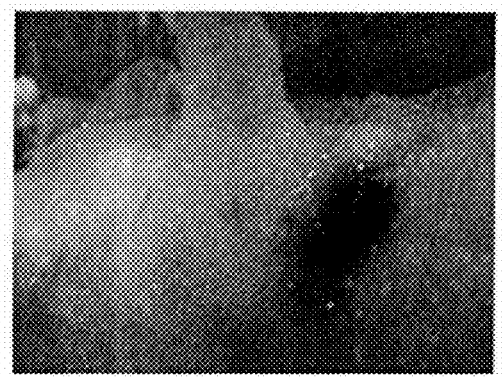
FIGS. 4A and 4B are images showing the results of spectral unmixing operations that used as spectral end-members the measured mouse autofluorescence signal spectrum and the mixed signal spectra detected over the region of the tumor, respectively.
Figure 4B:
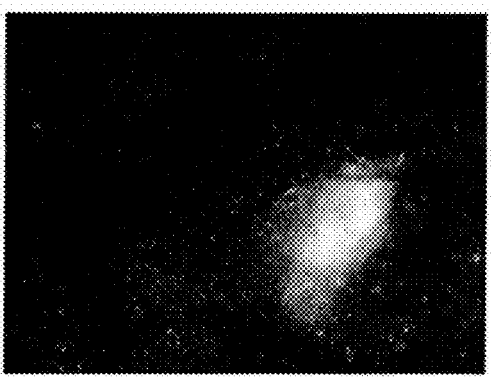

A good example of the pitfalls of these approaches is shown in FIGS. 4A and 4B. In the image of FIG. 2, a skilled user can faintly discern an area (of bluish hue in a corresponding color image) about where the lung should be. To an untrained eye, this irregularity caused by the tumor would be imperceptible. If one uses the signal spectra from surrounding areas as input spectra to represent autofluorescence, and the signal spectra from the area which looks like the tumor as input spectra to represent target fluorescence, and performs an unmixing using these input spectra, one arrives at the images shown in FIGS. 4A and 4B. FIG. 4A is the image of the portion of the field of view that most closely spectrally resembles the pixels corresponding to the area that was identified as autofluorescence. FIG. 4B is the image of the portion of the field of view that most closely spectrally resembles the pixels corresponding to the area that was identified as the tumor. The area associated with the tumor is well defined. However, there are problems with the images. For example, the "hole" left in the autofluorescence image (FIG. 4A), indicates that photons that were emitted from this area were inaccurately apportioned to the labeled tumor image.

If one wants to measure the amount of target fluorescence as a estimate of tumor size, this crosstalk can lead to significant error (e.g., a measured magnitude larger than the actual target fluorescence). Such an error occurs in this example because, even though the input spectrum used to represent the autofluorescence is primarily autofluorescence, the input spectrum representing the tumor is a mixture of target fluorescence and autofluorescence since the target compound and autofluorescing material are co-localized. To perform the unmixing correctly in this example, not only should the input autofluorescence spectrum be "pure," but the and input target fluorescence spectrum should also be "pure" (e.g., not being mixed with significant amounts of other component spectra, in this case autofluorescence).

Unmixing with Pure Spectra

Even though in some samples a component spectrum may not be represented in its "pure" form (i.e., substantially unmixed form, e.g., mixed with less than about 10% other components, or preferably less than about 1% other components) in any pixel's signal spectrum, an estimate for the pure component spectrum can in some cases still be obtained from the image cube data to use as an input spectrum for unmixing. For example, in some cases one component spectrum (e.g., corresponding to autofluorescence), identified as spectrum A, may be available in a "pure" form (e.g., from a pixel's signal spectrum or otherwise known or available). Another component spectrum, identified as spectrum B, however, may not be available in a "pure" form. In such cases, if spectrum B is represented in the image cube mixed only with spectrum A at one or more pixels that can be identified, then spectrum A can be subtracted from this mixed "A+B" spectrum to obtain a pure spectrum from B. The technique for more accurately estimating the pure spectra from the image cube is described further below. First, however, we describe an example in which spectral unmixing or decomposition of image cube data into contributions from estimates of pure spectra for different components of the sample was successfully used to image a target component in a deep tissue sample.

In this example, the specimen was illuminated and the illumination light from was blocked form entering the detector. This can be done using an illuminator such as the LT-9500 MSYS from Lighttools Research (Encinitas, Calif.) together with a longpass optical filter that transmits substantially all light $\lambda > 510$ nm, placed in the path of the objective.

The spectral imaging detector included a QImaging 1300C digital cooled CCD camera (Roper Scientific, Trenton N.J.) with a 55 mm F/2.8 Nikkor macro lens (Nikon USA, Melville N.Y.), to which a VARISPEC tunable optical filter (CRI Inc, Woburn Mass.) was coupled with a mounting adaptor. The VARISPEC filter is a computer-controlled optical filter with 25 nm bandpass and tunable center wavelength. These were connected to an IBM Thinkpad computer which controls the image acquisition and performs the data analysis. Communication is via an IEEE-1394 interface to the camera, and an RS-232 interface to the VARISPEC filter.

The VARISPEC filter uses nematic liquid crystal variable retarder elements to construct a tunable Lyot filter. The variable retarders are placed in optical series with fixed waveplates of quartz or other material, to produce a retardance that is well-known and electrically adjustable. Linear polarizers between successive stages of the filter act to block unwanted orders so only a single peak is transmitted, and out-of-band leakage can be reduced to 0.01% if desired. By choice of the retarder thicknesses, one may obtain bandwidths ranging from 0.1 nm to 50 nm or more. Tuning action is rapid (<50 ms) and there is no image shift from tuning, which is valuable for imaging applications.

Figure 5:
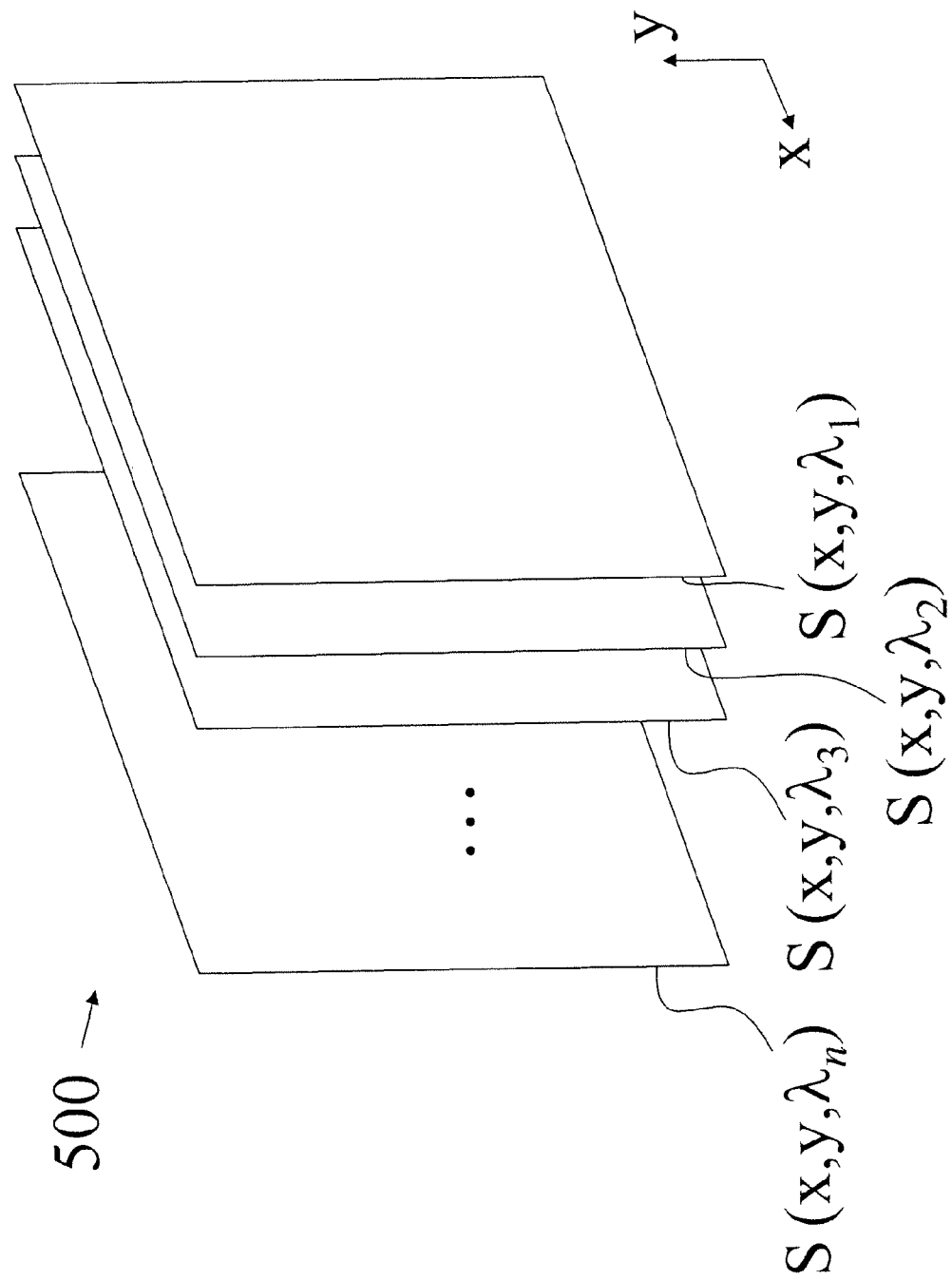
FIG. 5 is a set of images forming an image cube.
Figure 9:
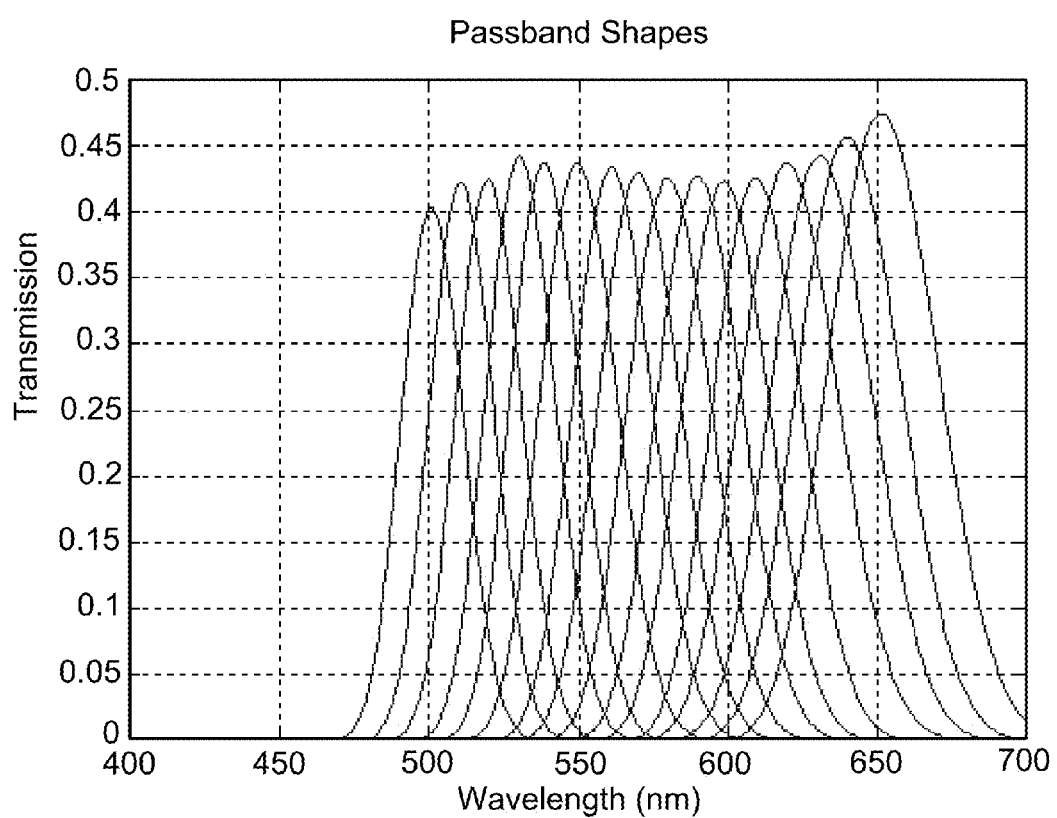
FIG. 9 is graph of the spectral properties of each spectral band in the embodiment of FIG. 8.

Referring to FIG. 5, the mouse of FIG. 2 was imaged by taking a sequence of images $S(x, y, \lambda_i)$ (for i=1 to n, the number of spectral settings) each recorded using a spectral weighting function $I_i$ determined by the VARISPEC filter, while the center wavelength of the VARISPEC filter was tuned from 500 nm to 650 nm. This sequence of images in FIG. 5 is an example of a spectral image cube 500. The different spectral spectral weighting functions (in this case, spectral passbands) are shown in FIG. 9. The result is an image cube 500, with a full two-dimensional image of the sample for a given center wavelength $\lambda_i$, and a full spectrum at a given pixel (x,y) in the images. The exact spectrum recorded at a given pixel depends on the amount of GFP and autofluorescence, and on the two spectra, as:

$$S(x,y,\lambda)=a(x,y)*F(\lambda)+b(x,y)*G(\lambda) \qquad [1],$$

where (x, y) indices are used to denote a given pixel location in the images, the asterisk "*" denotes multiplication, $\lambda$ is used to denote a given wavelength (or wavelength band) of emission or detection, and S(x, y, $\lambda$) denotes the net signal for a given pixel location and wavelength, F($\lambda$) denotes the emission spectrum of autofluorescence, G($\lambda$) denotes the emission spectrum of GFP, a(x, y) indicates the abundance of autofluorescence at a given (x, y) pixel location, and b(x, y) indicates the abundance of GFP at a given (x, y) pixel location.

Equation [1] states that the net signal from a given pixel location is the sum of two contributions, weighted by the relative amount of autofluorescence and GFP present. It is easier to see if one writes the above equation for a single pixel:

$$S(\lambda)=aF(\lambda)+bG(\lambda) \qquad [2].$$

F and G may be termed the spectral eigenstates for the system because they correspond to the pure spectra for the autofluorescence and GFP emission, which are combined in various amounts according to the amount of autofluorescence and GFP emission, to produce an observed spectrum or signal spectrum S. Thus, the signal spectrum is a weighted superposition corresponding to separate contributions from the autofluorescence and the GFP emission.

Now if the emission spectra of the autofluorescence and of the GFP are known (or can be deduced, as described below), one may invert equation [2] by linear algebra to solve for a and b, provided that the spectrum S has at least two elements in it; i.e. that one has data for at least two emission wavelengths λ. Equation [2] can be re-written as S=E A. Then we can write $$A = E^{-1} S \qquad [3],$$

where

A is a column vector with components a and b, and

E is the matrix whose columns are the spectral eigenstates, namely [F G].

Using equation [3] one can take the observed signal spectrum and calculate the abundance of the autofluorescence and of the GFP sources (e.g., the components that produce autofluorescence and GFP emission) at the corresponding pixel location. This process may be repeated for each pixel in the image, to produce an image of GFP that is free of contributions from autofluorescence. As a result, the detection level is greatly enhanced.

Note that the matrix E need only be inverted once for a given set of autofluorescence and target compound spectra, so the calculation of abundances is not burdensome and can be readily done in nearly real-time by a personal computer.

Figure 6:
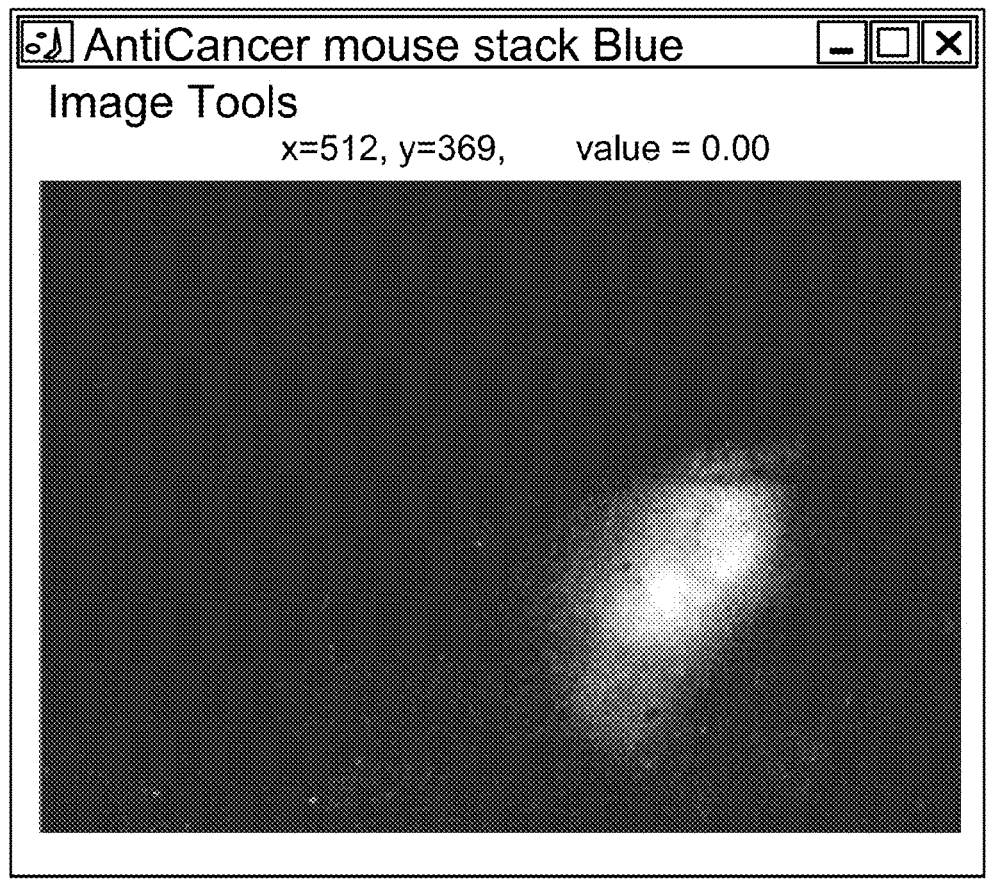
FIG. 6 is an image of the target compound emissions from the mouse of FIG. 2, with the autofluorescence signal removed using spectral techniques and end-member spectra that are estimated as well as directly measured.
Figure 7:
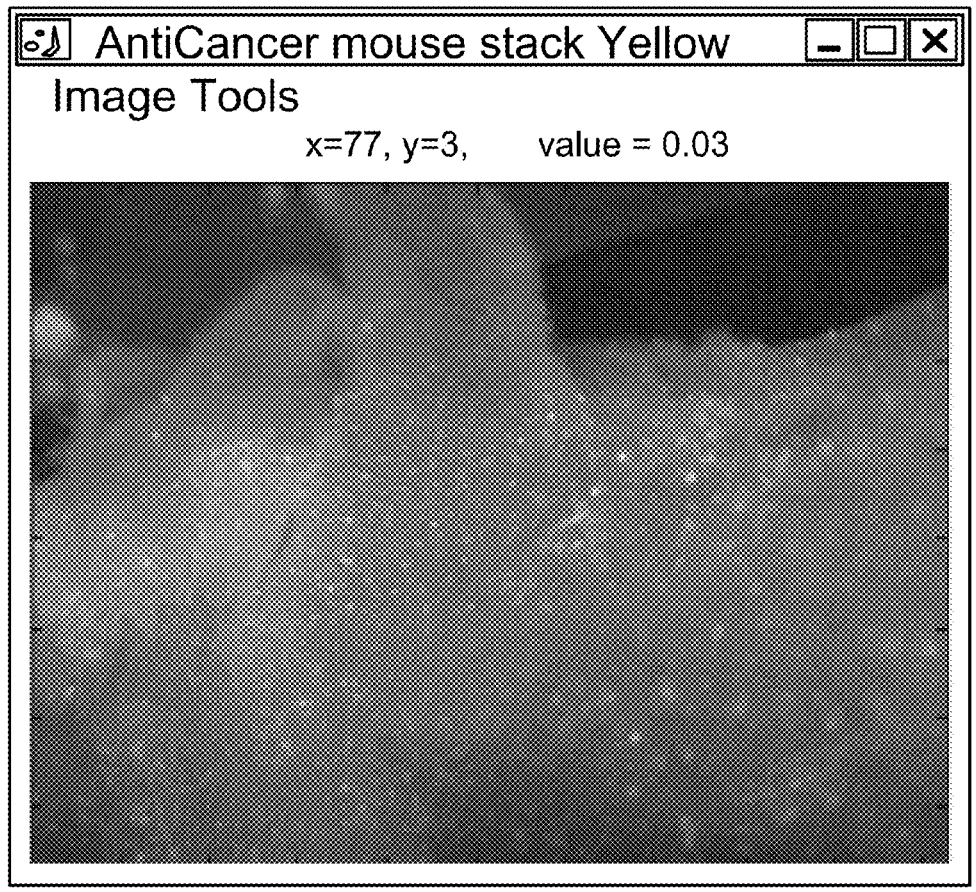
FIG. 7 is an image of the autofluorescence emissions from the mouse of FIG. 2, with the target compound emissions separated using spectral techniques and end-member spectra that are estimated as well as directly measured.

The results of this spectral unmixing process are shown in FIGS. 6 and 7, which present the abundance images for GFP and autofluorescence, respectively. As FIG. 6 shows, it is easy to detect the GFP once it is separated from the autofluorescence. The degree of improvement in the GFP image is striking. Also, one can see that the autofluorescence image (FIG. 7) is smooth and unaffected in the region where GFP is present, which is consistent with the fact that the presence of GFP in a deep tissue structure should not alter the amount of autofluorescence emission from the overlying dermal regions.

Figure 8:
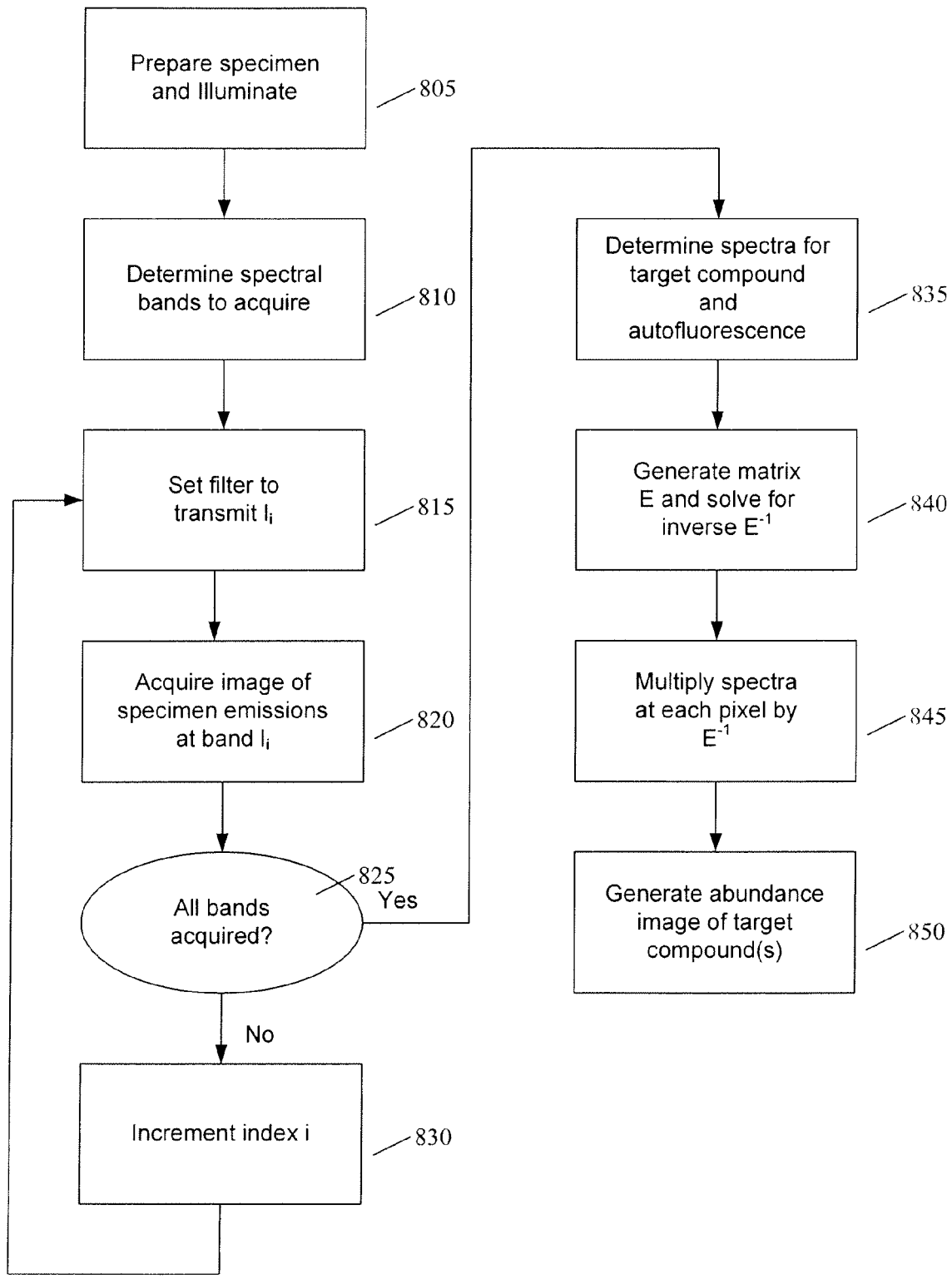
FIG. 8 is a flow-chart of one embodiment, based on acquisition of a spectral cube and subsequent analysis by linear unmixing.

Overall, an exemplary measurement and analysis process is shown as a block diagram in FIG. 8. The specimen is prepared and illuminated (step 805) and the spectral bands to be acquired determined (step 810). Then the spectral filter is set to transmit the spectral weighting function $I_i$, for example, a particular wavelength band (step 815), and an image corresponding to that spectral weighting function is acquired (step 820). The spectral filter is then set to the next spectral weighting function and the corresponding image acquired until all bands have been acquired (steps 825 and 830). The spectra for the target compound and the autofluorescence are then provided or otherwise determined (step 835). Based on the spectra, the matrix E is generated and its inverse determined (step 840). For each image pixel, the signal spectrum defined by the series of acquired images is then multiplied by the inverse matrix of E (step 845) to generate an abundance image of the target compound(s), i.e., the sample image (step 850).

In this example, spectral imaging permitted observation of structures in tissue lying ~2 mm within a living organism, where the overlying dermis is at least 300 microns thick and has significant autofluorescence. Spectral imaging has also been used to image structures at differing depths in other specimens, including non-mammalian specimens such as zebrafish. In the latter, the specimen is physically thinner, but once again there is the problem of autofluorescence arising from other layers in the specimen, which confounds the detection of target compounds in the interior of the specimen. While there are optical techniques for depth sectioning, such as confocal microscopy, the spectral imaging techniques described herein provide a simple and practical alternative.

An embodiment operating in the infrared range 600-1100 nm may also be constructed using a near-infrared VARISPEC filter such as the model VIS-NIR2-10-20HC.

Nothing about these techniques prevents one from viewing multiple target compounds per specimen (e.g., m target compounds). If we denote the number of spectral settings as n, matrix E becomes an n×m matrix instead of an n×2 matrix used in the above example. So, one can use these techniques to remove autofluorescence from a sample which contains two target compounds; or to remove two types of autofluorescence from a sample with one or more target compounds. In any case, the result is the isolation of the target compound(s) from the autofluorescence, and the ability to quantify one or all of these components.

The limit to the number of compounds that can be isolated, and to the signal to noise ratio generally, is given by the shot noise levels and the degree of spectral distinction between the emission spectra of the species being distinguished (including autofluorescence). One can describe the degree of correlation between two spectra by a spectral angle distance θ, defined by $$\theta = \arccos\left[(S_1 \cdot S_2)/(|S_1||S_2|)\right] \qquad [4].$$

Sets of spectra for which θ is small for two members are not as easily separated into their components. Physically, the reason for this is easily understood: if two spectra are only marginally different, it is harder to determine which species was present, and noise can easily change one's estimate of relative abundances. Criteria such as θ can be used to help decide what spectral bands are appropriate for a measurement, and one may try and select bands that yield a large θ whenever possible. Or, one may make an empirical study of what bands yield the best separation, by trial and error. It can be helpful to include more bands than would appear necessary from mathematical analysis alone, in order to reduce sensitivity to slight spectral shifts from the expected shapes, as may occur due to variation between specimens and the like.

Generally, the signal spectrum measured for each spatial location (i.e., pixel) in the sample and the estimates of the pure spectra used for the unmixing should typically include enough values to provide accurate information about the components of interest. For example, for a two-component sample analysis, it is preferable that there be at least three values (or more preferably, four or more values) corresponding to different spectral weighting functions (e.g., different spectral bands). As the number of components increase, the number of values for the signal and pure spectra should also increase.

It is worth considering the optical efficiency of the measurement apparatus in the above embodiment, to understand where the potential improvement provided by these techniques comes from. First, the lens used was an F/2.8 type instead of an F/1.2 or F/1.8 which is more typical for this work, and this choice results in 2.4-5.4× less light collection. Next, the VARISPEC filter has a transmission of approximately 25 percent, and collects over a 25 nm range, in contrast to a typical interference filter which has a transmission of 80 percent and collects over a 40 nm range. This further reduces the sensitivity by a factor of 5.1× compared to equipment that might be used for this work, for an overall reduction in light flux of 12.3×-27.8× compared to some alternatives of the art.

The CCD camera is cooled 25° below ambient to approximately 0° C., which is typical for an ordinary CCD sensor, unlike the sensors used in imaging stations such as the Chemi-Pro system from Roper Scientific (Trenton, N.J.), which is cooled with liquid nitrogen to attain temperatures 100° below ambient or lower.

As this suggests, the effectiveness of these techniques does not arise from extreme efficiency in the gathering or collection of light; rather it comes from using spectral selectivity to identify and remove the effects of background autofluorescence.

Figure 10:
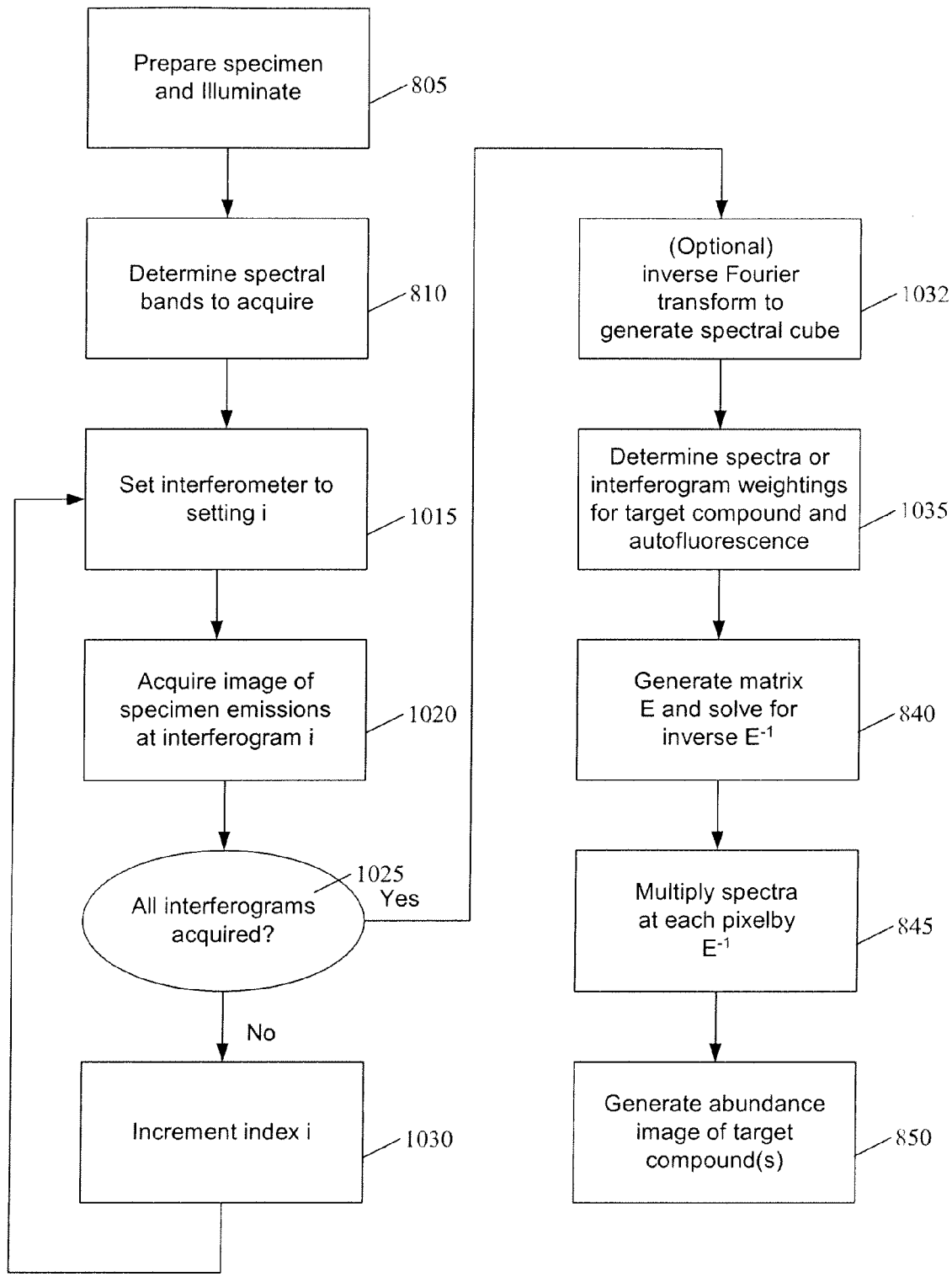
FIG. 10 is a flow-chart of yet another embodiment in which the spectral filtering is performed interferometrically.
Figure 11:
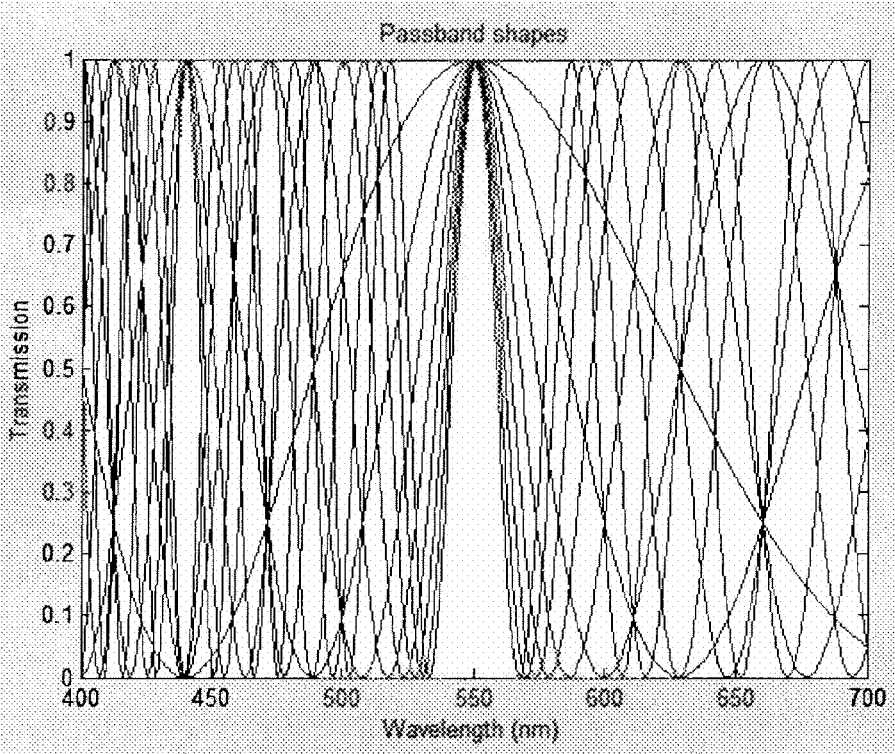
FIG. 11 is a graph of the spectral properties of the spectral weightings used in the embodiment of FIG. 10. Like reference symbols in the various drawings indicate like elements.

In other embodiments, the spectral weighting functions may be different from passbands. What is important is that the spectral weightings of the various images be different. For example, one could use an interferometer to acquire the spectral information, as shown in FIG. 10 in block-diagram form. The spectral response of the interferometer is shown in FIG. 11 for some selected values of path difference Z. Images thus obtained can be used for practicing the invention, either directly or after transforming from interferograms to spectra. The suitability of using the interferograms can be checked by looking at how well they distinguish between the species involved, which can be determined by measures such as cos θ or by experimental study.

The block diagram of FIG. 10 is similar to that of FIG. 8 except that: steps 815, 820, 825, and 830 are replaced with corresponding steps 1015, 1020, 1025, and 1030, which use a interferogram as the spectral weighting function rather than particular spectral bands; there is an optional step 1032, which describe Fourier transforming the spectrally filtered images to generate a spectral cube; and step 835 is replaced with step 1035 determines spectra or interferogram weightings for the target compound and the autofluorescence consistent with the form of the acquired data (and optional Fourier transform) for use in generating the matrix E.

The interferometer can be a mechanical type such as a Sagnac design, or it can be a birefringent interferometer as described in U.S. Pat. No. 6,421,131, "Birefringent interferometer". The latter uses fixed retarder elements such as quartz plates, together with switching apparatus, to make the retarders add or cancel one another, so that using these elements, along with variable retarder elements, one can produce any desired retardance within a wide range. When polarized light encounters this assembly, its polarization state is changed in a manner that depends on the wavelength of light, and this can be detected at an exit analyzer polarizer. The spectral response at any particular setting of the interferometer is a sinusoid in $1/\lambda$, after allowing for dispersion. By taking a sequence of readings at known retardance values, and performing a fourier transform, the spectrum of the light can be determined. Such apparatus can be used in imaging systems to obtain a spectrum at every point in an image, or simply to obtain a set of images with various sinusoidal spectral response functions in the members of the set.

More generally, any spectral imaging apparatus can be used provided that it yields adequate spectral information to distinguish emission by the target compound from background autofluorescence.

Accurately Estimating Pure Spectra

Figure 12:
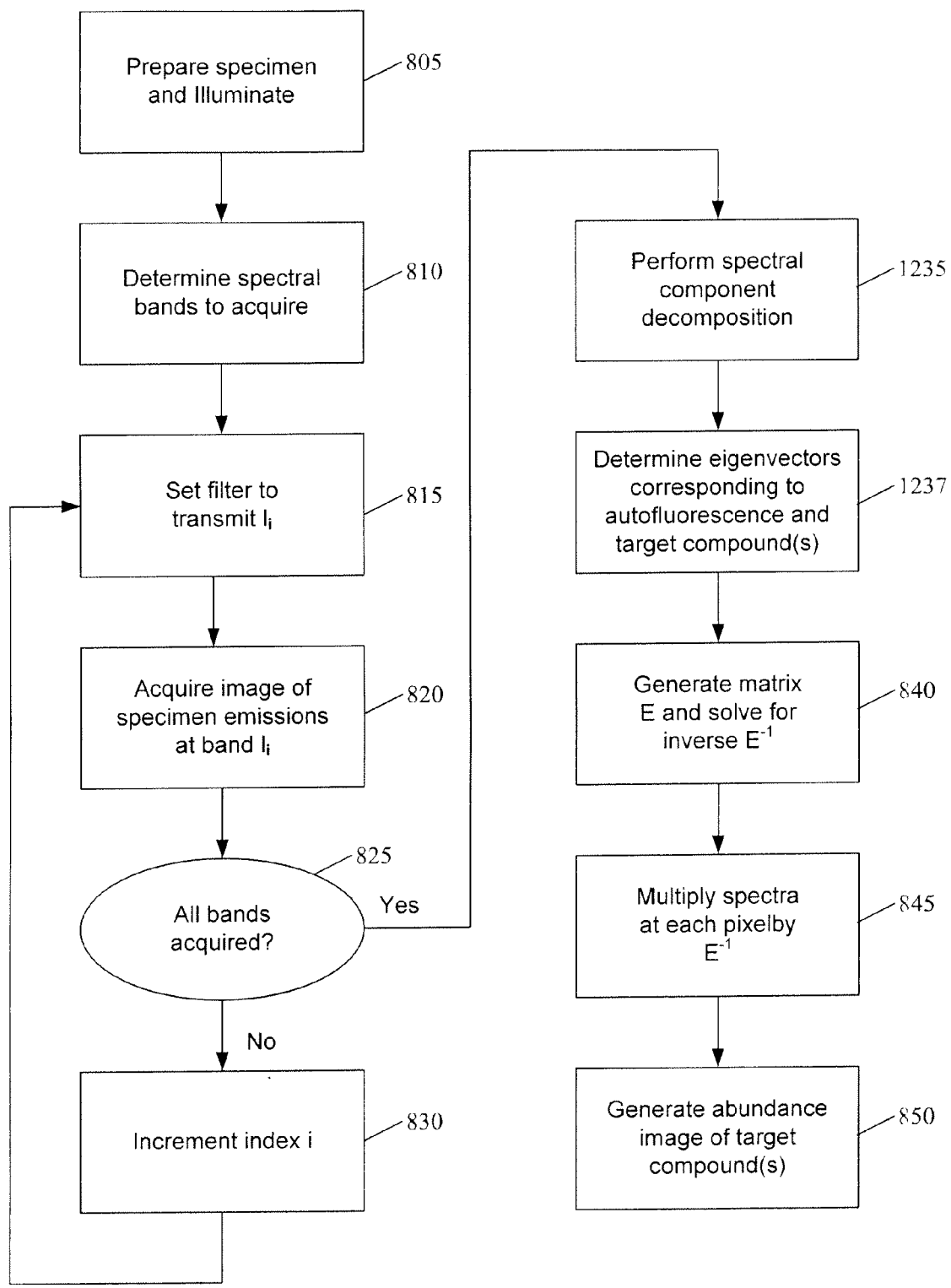
FIG. 12 is a flow-chart of another embodiment which incorporates spectral component decomposition to estimate the spectra of the autofluorescence and the target compound(s).

We now turn to the question of how the pure spectra F and G in the example above were determined, and more generally, how to accurately estimate pure spectra in the first place for use in the decomposition (i.e., unmixing) of the signal spectrum into their component spectra. FIG. 12 shows the steps in block-diagram form of a spectral unmixing technique in which one estimates the pure spectra for use as input spectra in the spectral unmixing. This step is sometimes referred to as spectral component decomposition to obtain pure input spectra. This is not to be confused with the decomposition (or unmixing) of the signal spectrum at each pixel into relative contributions of the pure input spectra in the unmixing. The block diagram is similar to that of FIG. 8, except that step 835 is replaced with performing a spectral component decomposition (step 1235) and determining eigenvectors corresponding to the autofluorescence and target compound(s) (step 1237) for use in the matrix E in step 840.

In general, any method may be used which yields an adequate estimate of the spectra involved. For some target compounds, there is a known spectrum for the material from published references. Alternatively, with a spectral imaging station as described herein, one may obtain the spectrum directly by placing a sample containing a sufficient concentration of the target compound in front of the imager and taking its spectrum. Conversely, it is often possible to image a region of the specimen where one has a priori knowledge that there is no target compound in that region, and in this way one can obtain an estimate of that component. Various data analysis techniques can be used in determining component spectra for spectral unmixing, such as principal component analysis (PCA), which identifies the most orthogonal spectral eigenvectors from an image cube, and yields score images showing the weighting of each eigenvector throughout the image. If PCA analysis is performed on an image that contains contributions from the target compound(s) and from the background autofluorescence, the vectors from PCA can be used to develop estimates of the spectra involved.

This may be done in combination with other mathematical processing, and there are other known techniques for identifying low-dimensionality spectral vectors, such as projection pursuit, a technique described in L. Jimenez and D. Landgrebe, "Hyperspectral Data Analysis and Feature Reduction Via Projection Pursuit", *IEEE Transactions on Geoscience and Remote Sensing*. Vol. 37, No. 6, pp. 2653-2667, November 1999. Other techniques include independent component analysis (ICA), projection pursuit, and end-member detection algorithms, for example.

These techniques are typically not well-suited to the applications in the life sciences. For example, some techniques are optimized for spectral imaging data sets that contain spectra with dense spectral shapes and well-defined narrow peaks. In some techniques the spectral ranges are large compared to the individual spectral features and peaks that are used for analysis. The presence of peaks, or the ratio of peaks may be then used to classify "end-members" to be separated. Unfortunately, the components in biological sample typically do not have such well-defined, narrow peaks.

Another issue with some techniques is that they output images related to spectra that are present in a pure form somewhere within the original image cube. In many cases in the life sciences, signal spectra present in the image cube are mixtures of components. In the case of the labeled tumor in a mouse, it is unlikely to ever find a location on the mouse where tumor exists and the autofluorescence does not. If the component of interest is not in a pure form somewhere in the original image cube, then it is unlikely that these techniques will output an image that accurately represents the abundance of the component of interest.

There are some techniques, sometimes call 'convex-hull' algorithms, that estimate what the true end-members are even if they do not exist in a pure form in the image, but the effectiveness is dependent on how close signal spectra in the image cube are to the end-members.

Another issue with some of the techniques is that they operate only in an unsupervised way which gives less opportunity to "steer" them in the right direction with information that is available from knowledge of the sample.

When most of these techniques are used with life sciences samples, the output images representing abundances of components often do not correlate well with known physiological or anatomical features in the samples. Some techniques work well in some cases, while others work well in other cases.

Figure 13A:
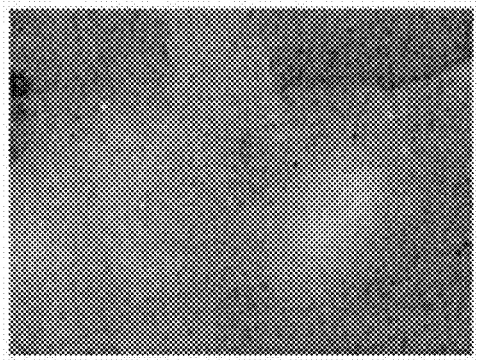
FIGS. 13A, 13B and 13C are exemplary images component abundance images generated by a typical non-life sciences end-member detection algorithm.
Figure 13B:
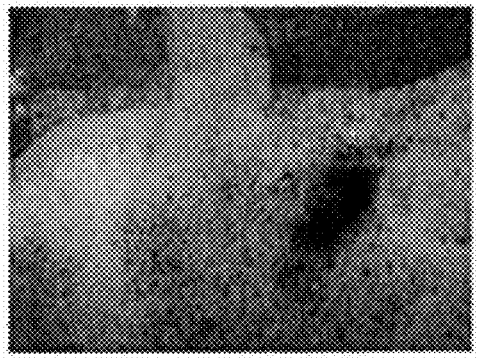
Figure 13C:
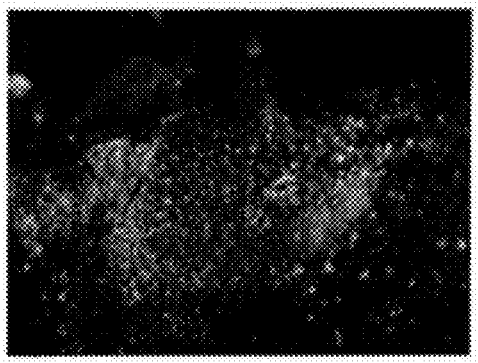

Shown in FIGS. 13A, 13B and 13C are exemplary component abundance images generated by a typical non-life sciences (e.g., remote sensing) end-member detection algorithm based on the image cube for the mouse of FIG. 2. Note that none of the output images appear to correspond with just the tumor or just the autofluorescence in the skin.

In the life sciences, and in particular fluorescence applications, the spectral features are broad and smooth, often spanning most of the detected spectral range. Usually the component spectrum (or spectra) of interest, the target fluorescence, shows up as a modification to the often larger and overwhelming autofluorescence signal. Key information used to analyze samples and determine composition lies in the individual detection and quantification of highly overlapping spectral components. Obtaining such information is better suited to techniques that are able to operate on subtle shifts in spectral shape. Techniques that are more appropriate for life sciences applications should be good at first rejecting the largest component, the autofluorescence, and then accurately separating away and quantifying smaller, overlapping spectral components. These characteristics are distinctly different from those of non-life sciences (e.g., remote sensing) applications.

We have discovered that one approach that does work well for accurately estimating pure spectra for deep tissue imaging is to use one estimate for the pure spectrum of one components that is easier to obtain and use it to help reveal the pure spectrum of another component from data in the image cube where both components are present. Implementations of this include techniques that calculate a remainder spectrum, which are described in greater detail further below.

Remainder Techniques

Some techniques for reducing the autofluorescence without having a priori knowledge of the target compound spectrum involve looking at the signal spectrum $S(\lambda)$ for a given pixel, and subtracting from it the maximum amount of autofluorescence $F(\lambda)$ while leaving the remaining signal that is positive definite in all spectral channels. That is, one defines a so-called remainder spectrum $R_a(\lambda)$ for each pixel:

$$R_a(\lambda)=S(\lambda)-aF(\lambda) \quad [5a],$$

and then selects the largest value of parameter a consistent with $R_a(\lambda)$ having a non-negative value in every spectral channel. The resulting spectrum $R_a(\lambda)$ is then used as the signal spectrum, expunged of autofluorescence. One may also make the determination of parameter "a" based not on strict non-negative criterion listed above, but on some related criteria that incorporates a small negative distribution, to account for considerations such as shot noise or detector noise. Additional examples of optimization criteria for removing the maximal amount of autofluorescence spectrum include using different error functions, some of which are described in more detail further below.

Alternatively, one may seek to determine the distribution of the target compound by a similar method when its emission spectrum is known, but the autofluorescence spectrum is not, by seeking to subtract off from $S(\lambda)$ the maximum amount of target emission $G(\lambda)$ consistent with a positive remainder, and then reporting the amount that was subtracted at each pixel as the image of the target compound. In this case, the remainder spectrum $R_b(\lambda)$ for each pixel is given by:

$$R_b(\lambda)=S(\lambda)-bG(\lambda) \quad [5b],$$

where one selects the largest value of parameter b consistent with $R_b(\lambda)$ having a non-negative value in every spectral channel.

Furthermore, the remainder technique described above in connection with Equations 5a and 5b can be expanded to cases where the spectra for one or more additional components of the sample are known, and one wants to remove their contribution to the signal. In such cases the remainder spectrum is rewritten to subtract a contribution of each such component from the observed signal based on the additional spectra and consistent with a positive remainder in each spectral channel.

The remainder technique assumes that an initial estimate for at least one of the component spectrum is provided. It can be provided by a prior knowledge or measurement, or it can be determined based on the image cube data itself. In the latter case, it can be determined by user-guidance (i.e., a supervised technique) or without user guidance (i.e., an unsupervised technique). For example, a user may be able to identify at least one region of the spectral image cube in which one component is nominally isolated, and thereby determined the pure spectrum for that component from the data in that region (e.g., by averaging the signal spectrum from the pixels in that region). In another example, without user-guidance, it might be assumed that because autofluorescence will dominant the spectral information in the image cube, one can simply average the spectral information in every pixel to determine an estimate for the pure spectrum of the autofluorescence.

Furthermore, the remainder spectrum can be calculated at one, some, or all of the pixels. For example, in the two-component case described above, the deep tissue image could be constructed directly from the remainder spectrum in each pixel, which is now assumed to be associated with only the target compound. In other examples, however, the remainder spectrum may be calculated for only one, or some pixels, as part of a more involved process for estimating pure spectra. Furthermore, the remainder technique may be applied to a preprocessed data set derived from the image cube. For example, the signal spectrum from some or all of the pixels in the image spectrum may be averaged to produce processed signal spectrum to which the remainder technique then is applied.

The more detailed technique below, which also involves calculating remainder spectra, is illustrative of these various possibilities. The techniques works well even with image cubes representative of the more difficult samples that one would encounter in fluorescence in-vivo imaging, fluorescence microscopy, and bright-field microscopy.

More Detailed Example of a Remainder Technique

Step 1: Determine Number of Components

A first step in some techniques for obtaining pure spectra is determining how many components are present in a given sample. Some remainder techniques include an automated step to delineate or identify areas of a sample that represent or indicate the location of what are probably individual components.

The remainder techniques are able to operate unsupervised, or with a user-provided spectrum as a starting point. In the unsupervised mode, a first iteration uses the average of all the signal spectra in the image cube as a first "spectral vector" to be subtracted. A best-fit approximation is performed at each pixel to determine a quantity of the pixel's signal spectrum that can be apportioned to the spectral vector. This quantity of the spectral vector is then subtracted out of the image cube data and a component image is generated representing the quantity that was subtracted. In subsequent iterations, it is assumed that the areas of highest intensity (after subtraction) are the next most spectrally pure component and those areas are used to obtain the next spectral vector. (The "intensity" at a pixel location is calculated by integrating the signal spectrum at that pixel over all wavelengths.) The number of iterations of subtracting spectral vectors that are performed can be specified up front, or can be continued until the amount of remainder signal left over is reduced below a specified percentage.

This approach has the advantage that often the spectral differences, that are "pealed" away and put into separate component images, are often very close to the pure spectra from the components. In cases where it is not, some user input is possible to guide it. For example, if the first spectral vector is the average spectrum of the whole image cube and is not close to one of the component spectra, which may happen for example with a shaved mouse instead of a nude mouse, then the user can point in the image at what should be autofluorescence, and the process can use that as the first spectral vector.

Figure 14A:
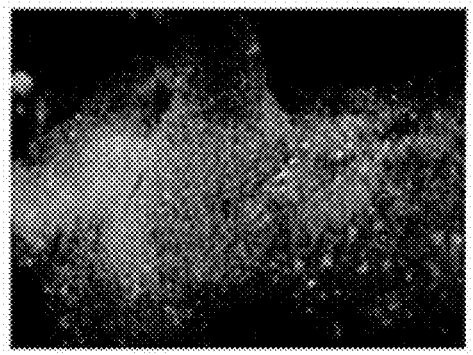
FIGS. 14A, 14B and 14C are output images generated by an unsupervised iterative remainder technique.
Figure 14B:
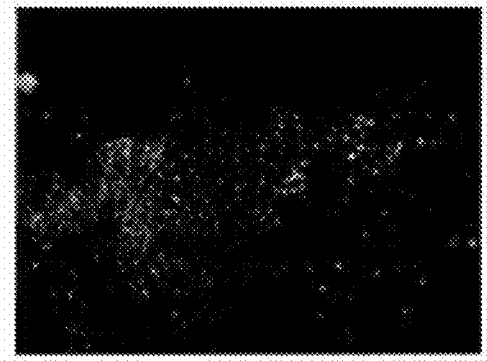
Figure 14C:
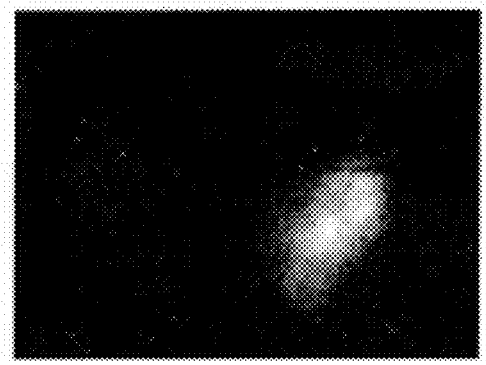

FIGS. 14A, 14B and 14C show output images generated by an unsupervised iterative remainder technique described above on the image cube for the mouse of FIG. 2. Note that these first three components correspond to features that make sense anatomically—an autofluorescence image from the skin (FIG. 14A), an autofluorescence image from the sebum around hair follicles (FIG. 14B), and the labeled tumor image (FIG. 14C) with relatively low signal from other components.

This spectral component decomposition technique is useful for providing component images that indicate to the user where the most significant components are and indicate from where in the image spectra should be extracted as input into the next iteration. Sometimes the decomposed component spectra are close enough to the actual spectra to be good estimates for the pure component spectra. If this is the case, the component images generated by the iterative remainder technique are sufficiently pure for whatever quantitative analysis is planned, such as tumor measurement or co-localization determination. However, sometimes, the decomposed component spectra are not accurate enough because the initial spectral vector uses the average spectrum from the entire image, and the component images represent some mixtures of components.

Step 2: Calculate Pure Component Spectra

After determining how many components are present in a given sample, pure component spectra can be calculated using the spectra extracted from the image cube data using the component images from the iterative remainder technique in step 1.

One way to do this, and to further improve the accurate apportioning of signal into the appropriate component images, is to use the component images from step 1 as a guide for further analysis. In other words, step 1 provides initial estimates for the pure spectra and component images based on those initial estimates, which can then be used to improve the initial estimates of the pure spectra.

For example, the user can choose component images from the iterative remainder technique in step 1, based on knowledge of the sample, that are thought to represent the a desired component (e.g., a component that includes a particular target compound) and an autofluorescence component that is co-localized with the desired component. The user first uses the component images to choose a region (e.g., a set of one or more contiguous or non-contiguous pixels) of the image cube corresponding to the autofluorescence component without the desired component, which is assigned to spectrum "A." The user then uses the component images to choose a region of one or more pixels that show strong intensity of the desired component (e.g., the tumor) along with the co-localized autofluorescence, which is assigned to spectrum "A+B."

These regions are then used to indicate pixel locations in the image cube data from which to draw the spectrum "A" $S_A(\lambda)$ and the spectrum "A+B" $S_{A+B}(\lambda)$ used by the remainder technique. This process can be repeated for multiple desired components. The remainder technique approximates a quantity Q of $S_A(\lambda)$ is present in $S_{A+B}(\lambda)$ using an optimized error function. This quantity of $S_A(\lambda)$ is then subtracted from $S_{A+B}(\lambda)$ to leave the difference spectrum $\Delta(\lambda)$ (with an optional constant offset C) whose optimized value is used to estimate the pure spectrum "B" $S_B(\lambda)$. The difference spectrum is given by:

$$\Delta(\lambda)=S_{A+B}(\lambda)-QS_A(\lambda)+C \quad [6].$$

The remainder technique determines optimized values for $Q=Q^{opt}$, and optionally $C=C^{opt}$, by minimizing an error function. Any of a variety of possible error functions may be used. One exemplary error function $err_1(\Delta)$ (where $\Delta \equiv \Delta(\lambda)$ is implicitly a function of $\lambda$) is given by:

$$err_1(\Delta)=(e^{-\Delta}+1)\Delta^2 \quad [7].$$

The remainder technique minimizes the average value of $err_1(\Delta)$ over $\lambda$. This error function $err_1(\Delta)$ is chosen to favor values of $\Delta$ that are positive, since a negative spectrum $S_B(\lambda)$ is not physically consistent. Alternatively, a minimum mean squared error (MMSE) criterion (e.g., $err_2(\Delta)=\Delta^2$) can be used along with a constraint that $\Delta$ be positive. However, such a strict constraint corresponds to a discontinuous error function that may not be as compatible with certain types of minimization techniques.

Other corrections can also be made. For example, a normalized error function:

$$err_3(\Delta)=err_1(\Delta)/[S_{A+B}(\lambda)+S_A(\lambda)] \quad [8]$$

can be used to correct for larger values of $err_1(\Delta)$ being caused by larger values of $S_A(\lambda)$ and $S_{A+B}(\lambda)$ that have the same relative magnitudes. A Value of $err_1(\Delta)$ (or of $err_3(\Delta)$) whose magnitude is below a noise threshold value can be set to zero.

Once the optimized values $Q^{opt}$ and $C^{opt}$ have been calculated, the pure spectrum $S_B(\lambda)$ is calculated as follows:

$$S_B(\lambda)=S_{A+B}(\lambda)-Q^{opt}S_A(\lambda)+C^{opt} \quad [9].$$

Step 3: Unmix Using Pure Component Spectra

After the pure component spectra are determined in step 2, unmixing can be performed on the image cube data using these pure component spectra. This is sometimes effective in simple systems if the components are known. However, it may not be optimal in some cases because it assumes all measured signal belong to one or another of the component images, thus forcing the sum of the signals in the unmixed images to equal the total detected signal. If the spectrum in the image cube at a particular pixel is made up of more components than is represented by the determined pure component spectra, then the unexpected component could and probably will be inaccurately apportioned into a target compound image.

To solve this problem, the iterative remainder technique of step 1 can be used in a "supervised" fashion where the spectra from Step 2 are used as input into each iteration to "strip out" component images. Each iteration produces a component image that corresponds to the spectrum that was used as an input for that iteration. This has the advantage that it does not force a sum of 100%, and leaves what is left over in a residual image for further processing if desirable.

Figure 15A:
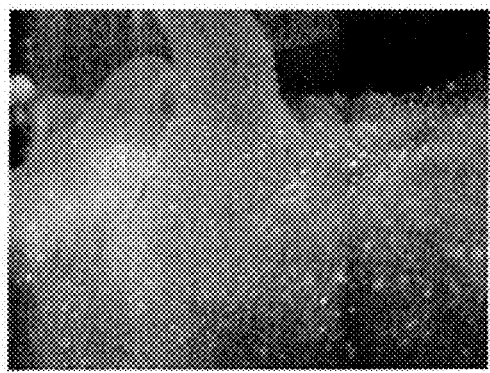
FIGS. 15A and 15B are output images generated by a supervised iterative remainder technique.
Figure 15B:
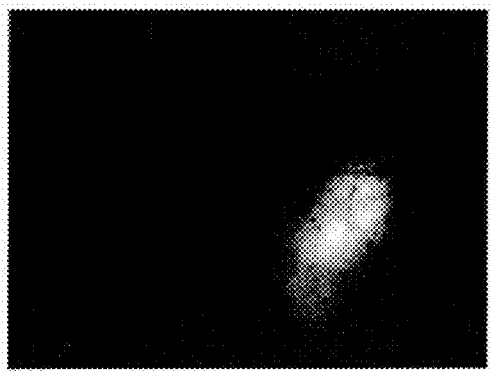

An example of how well this approach works is shown in FIGS. 15A and 15B. FIG. 15A shows the autofluorescence with uniform intensity across the area of the tumor, suggesting that the signals were accurately apportioned in the correct images. FIG. 15B shows the labeled tumor, appearing to be well isolated from other fluorescent components.

This capability can be configured in a variety of ways to provide very effective tools for examining and analyzing a sample. For example, it could be configured to remove components from a data set as they are pointed to by a user with an input device (e.g., a mouse). Spectral components both at the user selected locations and at other locations in the image cube with the same spectral signature can be removed. The spectrum for the selected component can be determined using Step 2, and removed as described in Step 3. Also, the residual image that contains signal that did not make it into a component image can be examined to see if there were any components that were not anticipated or known about.

Any of the steps by themselves and in any combination are useful. Steps 1 and 2 have value by themselves in many cases.

Figure 16:
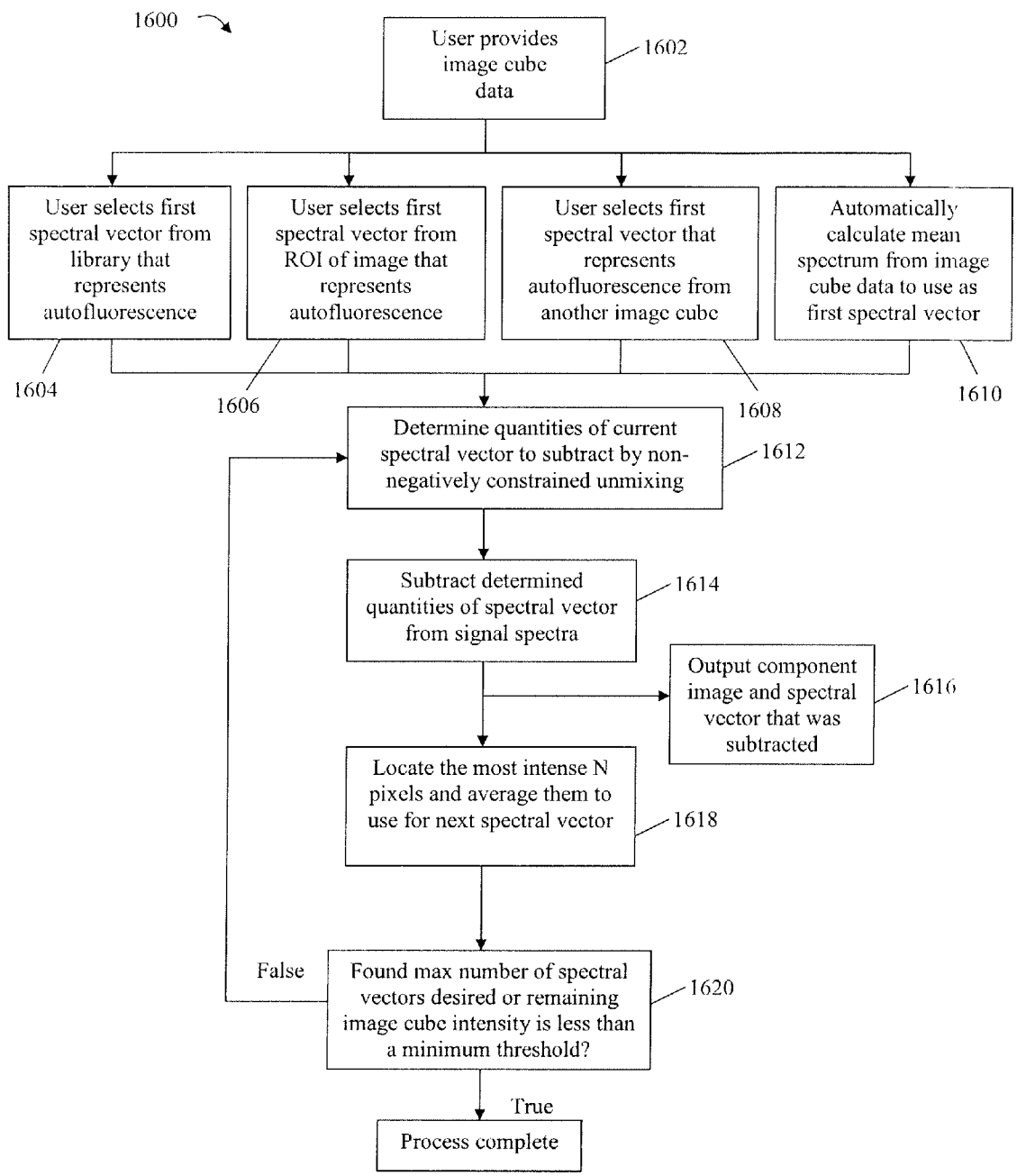
FIG. 16 is a flow-chart for a process for extracting spectral vectors.

FIG. 16 is a flow-chart diagram of a process 1600 that is illustrative of the iterative remainder technique in step 1 above process. Process 1600 extracts spectral vectors that can be used to calculate pure component spectra from image cube data. The resulting pure component spectra can be used as input spectra for unmixing and/or stored for later use in an spectral data library. A user provides 1602 image cube data either by acquiring the data from a sample or by loading previously acquired image cube data.

A first spectral vector is then provided by any of a variety of methods. A user may select 1604 a first spectral vector from a library of spectra (e.g., a library of spectra representing various types of autofluorescence for the types of samples being imaged). A user may select 1606 a first spectral vector from a region of interest (ROI) based on an image that represents autofluorescence (e.g., one of the images in the image cube). A user may select 1608 a first spectral vector from a previously acquired image cube. Alternatively, the process 1600 automatically determines 1610 a first spectral vector from the image cube data (e.g., by the averaging the signal spectra from all of the pixels to calculate a "mean spectrum").

The process 1600 then performs a non-negatively constrained unmixing on the image cube to determine 1612 a quantity for each pixel representing the amount of the current spectral vector that is to be subtracted from that pixel's signal spectrum. At each pixel, the process 1600 subtracts 1614 the largest amount of the current spectral vector from the signal spectrum that can be subtracted without making the resulting remainder spectrum become negative at any wavelength. The process outputs 1616 a component image representing the quantity of the current spectral vector that was subtracted at each pixel and the corresponding current spectral vector that can be used in subsequent processing (e.g., information provided in a component image can be used to locate preferred spectra for input into the PCSC process).

The process 1600 then determines the next spectral vector from a set of one or more pixels that represent the largest "error" in the resulting "remainder image cube" (i.e., an image cube having the remainder spectra calculated above as signal spectra). For example, the process 1600 selects 1618 the next spectral vector as the average of the spectra of the most intense N pixels in the remainder image cube (e.g., N=25). Alternatively, the process 1600 selects the most intense N pixels and then chooses a subset R of the N pixels that are within a specified spectral angle distance θ of the most intense of the N pixels.

The process 1600 repeats these steps 1612, 1614, 1616 and 1618 until a minimum intensity level has been reached or a specified number of spectral vectors have been found 1620.

Additional Embodiment

The techniques above are applicable to a wide range of deep tissue samples, including, for example, living organisms, mammals (e.g., humans, rodents, etc.), subdermal tissues, organs, etc. For example, the sample can also be a zebrafish in an aqueous sample stage. More generally, the techniques above, for example the techniques for estimating pure spectra, can be used for non-deep-tissue biological samples, including, e.g., tissue slices, cells, microscope slide samples.

The sample holder will depends on sample but, in addition to including sample holders for holding an animal such as a mouse, they can include, for example, a culture dish, a microtitre plate, a protein array, a DNA array, a gel plate, or a tissue micro array plate. For in vivo imaging, the sample may be a surface on which a subject or animal sits, rests, or is immobilized.

Of course, target compounds different from GFP may be used. For example, the same apparatus may be used to view a mouse, or any other sample, that has been transfected to express either the yellow fluorescent protein (YFP) or the red fluorescent protein (RFP), or both, and produces images of the target compound(s) after removal of the autofluorescence signal. There are also mutant strains developed which may also be used. Any of these may be combined with the GFP when that produces useful results. Also, for examples, the target compound can be based on quantum dots, which of size distributions tailored to provide various spectral signatures.

In addition to a tunable liquid crystal spectral filter, other embodiments for the spectral filtering are possible, including, for example, an acousto-optical tunable spectral filter, a set of spectral filters, a spectral filter wheel, a dispersive prism, a grating, a spectrometer, or monochromator. For example, one could use a motorized filter wheel containing a plurality of bandpass filters. Yet another embodiment could use a split-image system from Optical Insights (Tucson, Ariz.) to view the specimen in four spectral bands at once, albeit with lower spatial resolution. The bands are chosen to give a spectrum that distinguishes between the target compound and background autofluorescence, i.e. to have cos θ that is significantly different from 1, preferably 0.8 or less.

There are also numerous techniques for obtaining spectrally resolved images. For example, some of these techniques include: "Raster-scanning" systems where each pixel is illuminated and the emission spectrum acquired, and the image is obtained by sequentially acquiring each pixel; "Push-broom" systems, where spectra are acquired from a line of the sample by taking the emission light from a line, or strip, of the sample, and putting it through an imaging grating to acquire a line of spectra from the sample, and then the sample is moved along under the imaging system (or the imaging system is moved over the sample) and another line is acquired until an image is built-up; and "True-imaging" systems, that take spectrally resolved images of a sample.

Figure 17:
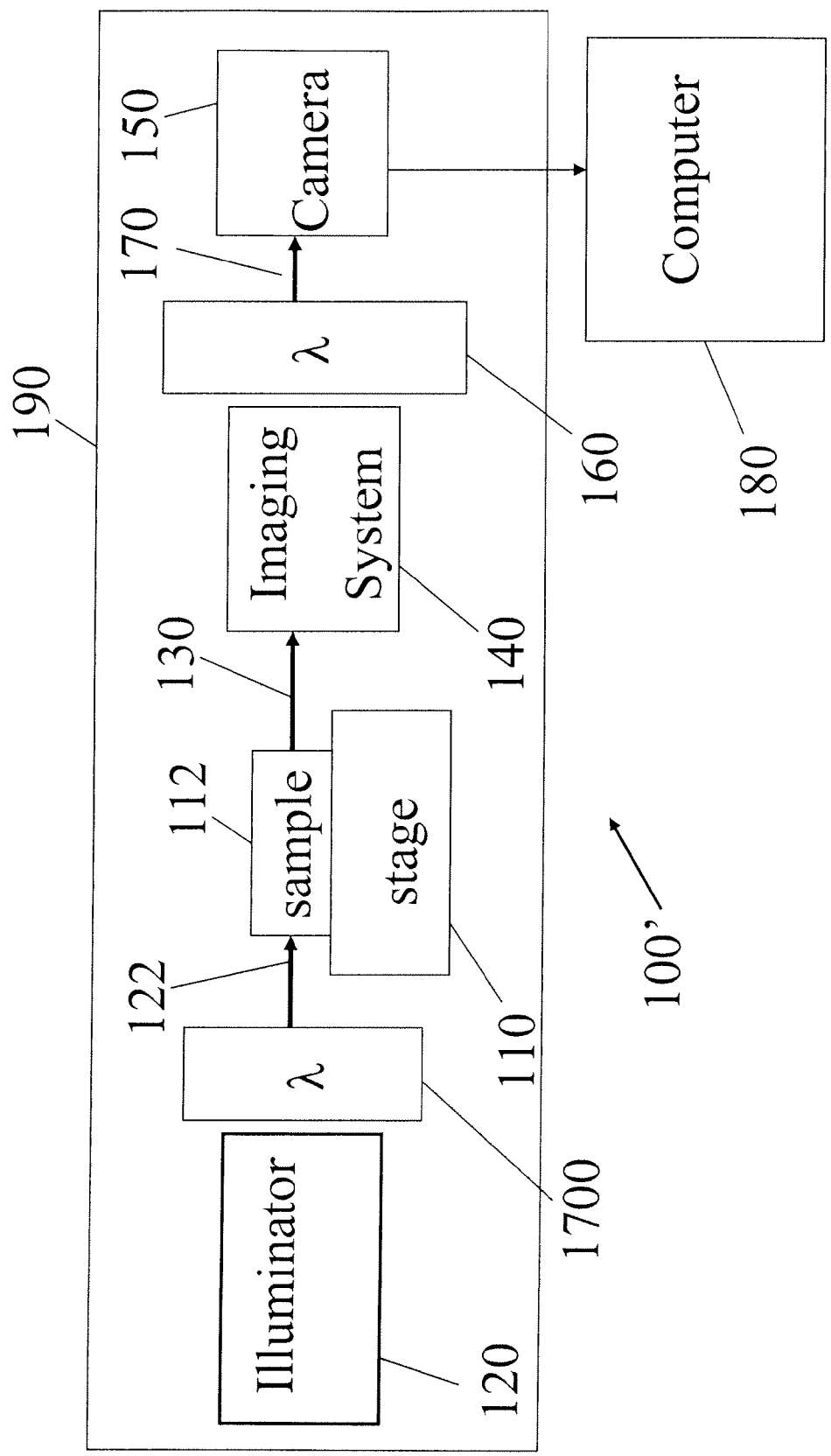
FIG. 17 is a schematic diagram of a spectral imaging system.

Furthermore, while the above techniques and analysis have focused on situations in which the light coming from the sample is spectrally filtered to discriminate between selected components. The same algorithms can be applied to the situation in which the light used to illuminate the sample is spectrally filtered to discriminate between selected components. In other words, rather than focus on the emission spectra of the different components in the sample, one can focus on the excitation spectra of the different components in the sample. In such embodiments, the light measured from a particular region of the sample is spectrally resolved as a function of different spectral weighting functions for the excitation light. The basic principle for spectral unmixing remains the same, however, because the intensity of the measured light at for each spectral weighting function will include contributions from different components according to the degree to which those components are excited by light at corresponding to that spectral weighting function. For example, FIG. 17 shows a spectral imaging system 100' that includes an excitation side spectral filter 1700 for switching among multiple excitation wavelength bands. The resulting image cube data can be processed as described above where, for example, the wavelength $\lambda$ in equation [1] is used to denote a given wavelength (or wavelength band) of excitation. The illumination source for such technique may be a broadband source which is then spectrally filtered as above, or an array of sources having different spectral emission, such as an LED or diode array. Such techniques are also further described in U.S. application Ser. No. 10/226,592 (Publication No. US-2003-0081204-A1), which is incorporated herein by reference. Other techniques for providing excitation light can also be used such as those described in U.S. application Ser. No. 10/163,233 (Publication No. US-2003-0223248-A1), incorporated herein by reference.

Furthermore, in some embodiments, data may be collected as a function of both the excitation and emission wavelengths.

Though the techniques were described above in terms of measuring fluorescence, the same techniques can be applied to determining concentration of one or more target compounds based on other types of light measurements. The light emission phenomena can be based on any of fluorescence, transmission, reflectance, scattering, Raman scattering, or phosphorescence. For example, nanoparticles available from Nanoplex Technologies Inc., (www.nanoplex.com) in Menlo Park, Calif. can be used as target compounds that provide Raman emission. Some of these measurements may include conversion of measured signals into other units. What is important is that the measurement provide spectral information useful to distinguish a desired signal corresponding to a target compound from other signal components, and thus to improve the measurement integrity and sensitivity.

For example, some embodiments involve the transmission of light through an absorbing medium. Under such conditions, the intensity of measured light is reduced with an exponential dependence upon target compound concentration. However, a transform to "optical density" (e.g., by applying a logarithm function) enables linear unmixing techniques. Such optical density techniques are further described in U.S. application Ser. No. 10/226,592 (Publication No. US-2003-0081204-A1), incorporated herein by reference. Other embodiments may include measurements based on brightness ratios at several selected wavelengths or wavelength bands.

Embodiments for estimating pure spectra may also include unsupervised techniques such as cluster analysis. Cluster analysis identifies regions of the sample that have a similar spectral response by clustering the spectra such that the differences in the intra-cluster spectral responses are minimized, while simultaneously maximizing the inter-cluster differences between spectral responses. In this implementation, the results of a cluster analysis include, for each cluster, the cluster centroid spectrum (viz., the weighted mean spectrum for the cluster), and the corresponding cluster membership map (viz., the spatial distribution of the cluster). Taken together, they answer two commonly posed questions about spectroscopic imaging: where did the different types of spectra occur, and what were the spectral characteristics of the spectra.

Once regions with specific components have been identified through exploratory unsupervised analyses, the location of those components can be more thoroughly investigated using a supervised classifier. Training set spectra used for the supervised classifier can be extracted from regions identified by the unsupervised analyses as containing a specific component, or they can be selected from the data set using previous knowledge of the composition of the sample. The supervised classifier can then refine the segmentation of the image by locating regions which have spectral profiles matching the training spectra. Unsupervised analyses, combined with a supervised classifier, provide a means of locating the constituent components without a priori knowledge of the number or nature of the components present in the sample. In addition, using the spectra selected for the training set as targets in library spectral search routines would also enable an automated identification of the components.

Supervised pattern recognition methods are potentially better suited to the development of clinically or industrially useful data analysis methods. Supervised pattern recognition techniques such as linear discriminant analysis (LDA) or neural networks make use of the fact that the investigator often has a substantial amount of spectroscopic data available (either biochemical or clinical). For example, the investigator may know that spectra arise from well-defined sample components or tissue types. This information may then be used to train a LDA algorithm to recognise the particular combinations of variables (peak frequencies, bandwidths, relative intensities, etc.) in the spectra that are characteristic of these sample components or tissue types.

The spectral analysis and construction of the sample image can be implemented in hardware or software, or a combination of both. The electronic processing can be implemented in computer programs using standard programming techniques following the methods described herein. Program code is applied to input data to perform the spectral unmixing functions described herein and generate output information such as the sample image. The output information is applied to one or more output devices such as a display monitor.

Each program is preferably implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., CD-ROM or magnetic diskette) readable by a general or special purpose programmable computer, for configuring and operating the computer when the storage media or device is read by the computer to perform the procedures described herein. The computer program can also reside in cache or main memory during program execution. For example, computer 180 in FIG. 1 may includes a processor, an input/output control card, a user interface, such as a keyboard and monitor, and a memory. A program stored on a computer-readable medium is stored in the computer memory, and when executed, the program causes the processor to carry out the steps of analyzing the spectrally filtered images.

Additional aspects, features, and advantages are within the scope of the following claims.

What is claimed is:

1. A method for spectrally unmixing light data corresponding to light emitted from multiple different fluorescent light sources internal to an animal, the method comprising:
    selecting an excitation wavelength band for excitation light provided to the animal;
    selecting an emission wavelength band that limits light wavelengths collected from the animal;
    providing excitation light, into the animal, that is limited to the excitation wavelength band;
    capturing a first image of at least a portion of the animal, where the first image includes light data that is limited in wavelength to the emission wavelength band and corresponds to light emitted by the multiple different fluorescent light sources in the emission wavelength band internal to the animal;
    changing the excitation wavelength band and/or the emission wavelength band;
    capturing at least one additional image of at least the portion of the animal that uses a different combination of excitation wavelength band and emission wavelength band for each additional image, where each additional image includes light data that corresponds to light emitted by the multiple different fluorescent light sources internal to the animal and is limited in wavelength to the emission wavelength band of the different combination; and
    using an iterative solution process, unmixing spectra for the multiple fluorescent light sources internal to the animal the light data in the images to provide a spectrum for each light source of the multiple different fluorescent light sources,
    wherein each spectrum provides wavelength-dependent excitation and/or emission information about the corresponding fluorescent light source.

2. The method of claim 1 further comprising determining the number of fluorescent light sources before unmixing the light data in the images spectra for the multiple fluorescent light sources.

3. The method of claim 1 wherein a total number of images captured by the camera is no less than the number of fluorescent light sources in the animal.

4. The method of claim 1 wherein the different combination for each additional image uses a common excitation wavelength band and multiple emission wavelength bands.

5. The method of claim 1 wherein the different combination for each additional image uses a common emission wavelength band and multiple excitation wavelength bands.

6. The method of claim 1 where the excitation light is provided into the animal from a portion of the animal that is visible to the camera during image capture.

7. The method of claim 1 where the excitation light is provided into the animal from a portion of the animal that is not visible to the camera during image capture.

8. The method of claim 1 wherein the iterative solution process also outputs a spatial distribution map for each of the multiple fluorescent light sources internal to the animal, where each spatial distribution map provides a two dimensional representation of a distribution of a fluorescent light source in the animal.

9. The method of claim 1 further comprising providing an initial estimate of each spectrum for the multiple fluorescent light sources.

10. The method of claim 1 further comprising applying a constraint to the iterative solution process.

11. The method of claim 10 wherein the constraint includes a spectral constraint.

12. The method of claim 11 wherein the spectral constraint includes a non-negativity constraint that limits the spectrum for each light source to a non-negative number.

13. The method of claim 10 wherein the constraint includes a spatial distribution map constraint.

14. The method of claim 13 wherein the spatial distribution map constraint includes a region of interest constraint that limits spatial area for a fluorescent light source in a spatial distribution map produced by the iterative solution process.

15. The method of claim 1 wherein the multiple fluorescent light sources include tissue autofluorescence in the animal.

16. Logic encoded in one or more non-transitory storage devices for execution and, when executed, operable to spectrally unmix light data corresponding to light emitted from multiple different fluorescent light sources internal to an animal, the logic including:
    instructions for selecting an excitation wavelength band for excitation light provided to the animal;
    instructions for selecting an emission wavelength band that limits light wavelengths collected from the animal;
    instructions for providing excitation light, into the animal, that is limited to the excitation wavelength band;
    instructions for capturing a first image of at least a portion of the animal, where the first image includes light data that is limited in wavelength to the emission wavelength band and corresponds to light emitted by the multiple different fluorescent light sources in the emission wavelength band internal to the animal;
    instructions for changing the excitation wavelength band and/or the emission wavelength band;
    instructions for capturing one or more additional images of at least the portion of the animal, using a different combination of excitation wavelength band and emission wavelength band for each additional image, where each additional image includes light data that corresponds to light emitted by the multiple different fluorescent light sources internal to the animal and is limited in wavelength to the emission wavelength band of the different combination; and
    instructions for unmixing the light data in the images spectra, using an iterative solution process, for the multiple fluorescent light sources internal to the animal to provide a spectrum for each of the multiple different light fluorescent sources,
    light source wherein each spectrum provides wavelength-dependent excitation and/or emission information about the corresponding fluorescent light source.

17. A method for spectrally unmixing light data corresponding to light emitted from multiple different light sources internal to an animal, the method comprising:
    selecting an emission wavelength band that limits light wavelengths collected from the animal;
    capturing a first image of at least a portion of the animal, where the first image includes light data that is limited in wavelength to the emission wavelength band and corresponds to light emitted by the multiple different light sources in the emission wavelength band internal to the animal;
    changing the emission wavelength band;
    capturing one or more additional images of at least the portion of the animal, using a different emission wavelength band for each additional image, where each additional image includes light data that corresponds to light emitted by the multiple different light sources internal to the animal and is limited in wavelength to the different emission wavelength band; and using an iterative solution process, unmixing the light data in the images spectra for the multiple light sources internal to the animal to provide an emission spectrum for each of the multiple different light sources light source, wherein the iterative solution process implements a multivariate curve resolution and iteratively solves for each emission spectrum a spectrum of each of the multiple light sources using finishing criteria, wherein each emission spectrum provides wavelength-dependent emission information about the corresponding light source.

18. The method of claim 17 further comprising selecting an excitation band for excitation light provided to the animal and providing excitation light, into the animal, that is limited to the excitation wavelength band, when the multiple light sources include a fluorescent light source.

19. The method of claim 17 wherein the iterative solution process also outputs a spatial distribution map for each of the multiple light sources internal to the animal, where each spatial distribution map provides a two dimensional representation of a distribution of a light source in the animal.

20. The method of claim 17 wherein the finishing criteria uses an alternating least square method.

21. An imaging system for imaging an animal, the imaging system comprising:

an imaging chamber that includes a set of walls and a door that enclose an interior cavity, a stage configured to support the animal within the interior cavity, a camera, and a fluorescent excitation source; and a processing system including a processor and non-transitory memory, the memory including instructions for selecting an excitation wavelength band for excitation light provided to the animal, instructions for selecting an emission wavelength band that limits light spectra wavelengths collected from the animal, instructions for obtaining one or more fluorescent images using the camera, and instructions for unmixing the fluorescent images spectra, using an iterative solution process, for the multiple fluorescent light sources internal to the animal to provide a spectrum for each of multiple different fluorescent light source sources internal to the animal, wherein each spectrum provides wavelength-dependent excitation and/or emission information about the corresponding fluorescent light source.

22. The imaging system of claim 21 further comprising:

an excitation filter configured to intercept excitation light produced by the fluorescent excitation source before the excitation light reaches the animal; and an emission filter configured to intercept emission light emitted from the animal before the emission light reaches the camera.

23. The imaging system of claim 21 further comprising a structured light projector.

24. The imaging system of claim 21 wherein the fluorescent excitation source is below the stage.

* * * * *